US008889743B2

(12) United States Patent
Davey et al.

(10) Patent No.: US 8,889,743 B2
(45) Date of Patent: Nov. 18, 2014

(54) INHIBITION OF FILOVIRUS ENTRY INTO CELLS AND USES THEREOF

(75) Inventors: Robert A. Davey, Galveston, TX (US); Andrey A. Kolokoltsov, Galveston, TX (US); Mohammad F. Saeed, League City, TX (US)

(73) Assignee: Board of Regents, University of Texas System, Austin, TX (US)

( * ) Notice: Subject to any disclaimer, the term of this patent is extended or adjusted under 35 U.S.C. 154(b) by 291 days.

(21) Appl. No.: 12/653,916

(22) Filed: Dec. 21, 2009

(65) Prior Publication Data

US 2011/0152344 A1     Jun. 23, 2011

Related U.S. Application Data

(63) Continuation-in-part of application No. PCT/US2008/007747, filed on Jun. 20, 2008.

(60) Provisional application No. 60/936,426, filed on Jun. 20, 2007.

(51) Int. Cl.
| | |
|---|---|
| A61K 31/135 | (2006.01) |
| A61K 31/18 | (2006.01) |
| A61K 31/277 | (2006.01) |
| A61K 31/713 | (2006.01) |
| A61K 31/4741 | (2006.01) |
| A61K 31/366 | (2006.01) |
| A61K 31/554 | (2006.01) |
| A61K 33/00 | (2006.01) |
| A61K 31/435 | (2006.01) |
| A61K 31/5377 | (2006.01) |

(52) U.S. Cl.
CPC .............. *A61K 31/366* (2013.01); *A61K 31/18* (2013.01); *A61K 31/277* (2013.01); *A61K 31/713* (2013.01); *A61K 31/4741* (2013.01); *A61K 31/554* (2013.01); *A61K 33/00* (2013.01); *A61K 31/435* (2013.01); *A61K 31/5377* (2013.01)
USPC .......................................................... 514/647

(58) Field of Classification Search
USPC ......................................................... 514/647
See application file for complete search history.

(56) References Cited

U.S. PATENT DOCUMENTS

| | | | | | |
|---|---|---|---|---|---|
| 4,800,081 | A | * | 1/1989 | Albrecht et al. | 424/607 |
| 5,053,419 | A | * | 10/1991 | Lipton | 514/356 |
| 2002/0107193 | A1 | * | 8/2002 | Glazner | 514/12 |
| 2007/0003608 | A1 | * | 1/2007 | Almond et al. | 424/450 |

FOREIGN PATENT DOCUMENTS

| | | | |
|---|---|---|---|
| WO | WO 0113907 | A2 * | 3/2001 |
| WO | WO 2007008665 | A1 * | 1/2007 |

OTHER PUBLICATIONS

Fields et al. Filds Virology, Lippincott Williams & Wilkins, 1995, pp. 53.*
Ozaki et al. "inhibitory mechanism of xestoponin-C on contraction and ion channels in the intestinal smooth muscle," British Journal of Pharmacology (2002) 137, 1207-1212.*

* cited by examiner

*Primary Examiner* — Shengjun Wang
(74) *Attorney, Agent, or Firm* — Winstead PC

(57) ABSTRACT

The present invention discloses method to treat infections caused by filovirus. Such a method comprises blocking the PI3 kinase pathway or the calcium-associated pathway at the gene or protein level. Also disclosed herein are the compounds useful in the treatment of filoviral infection.

2 Claims, 13 Drawing Sheets

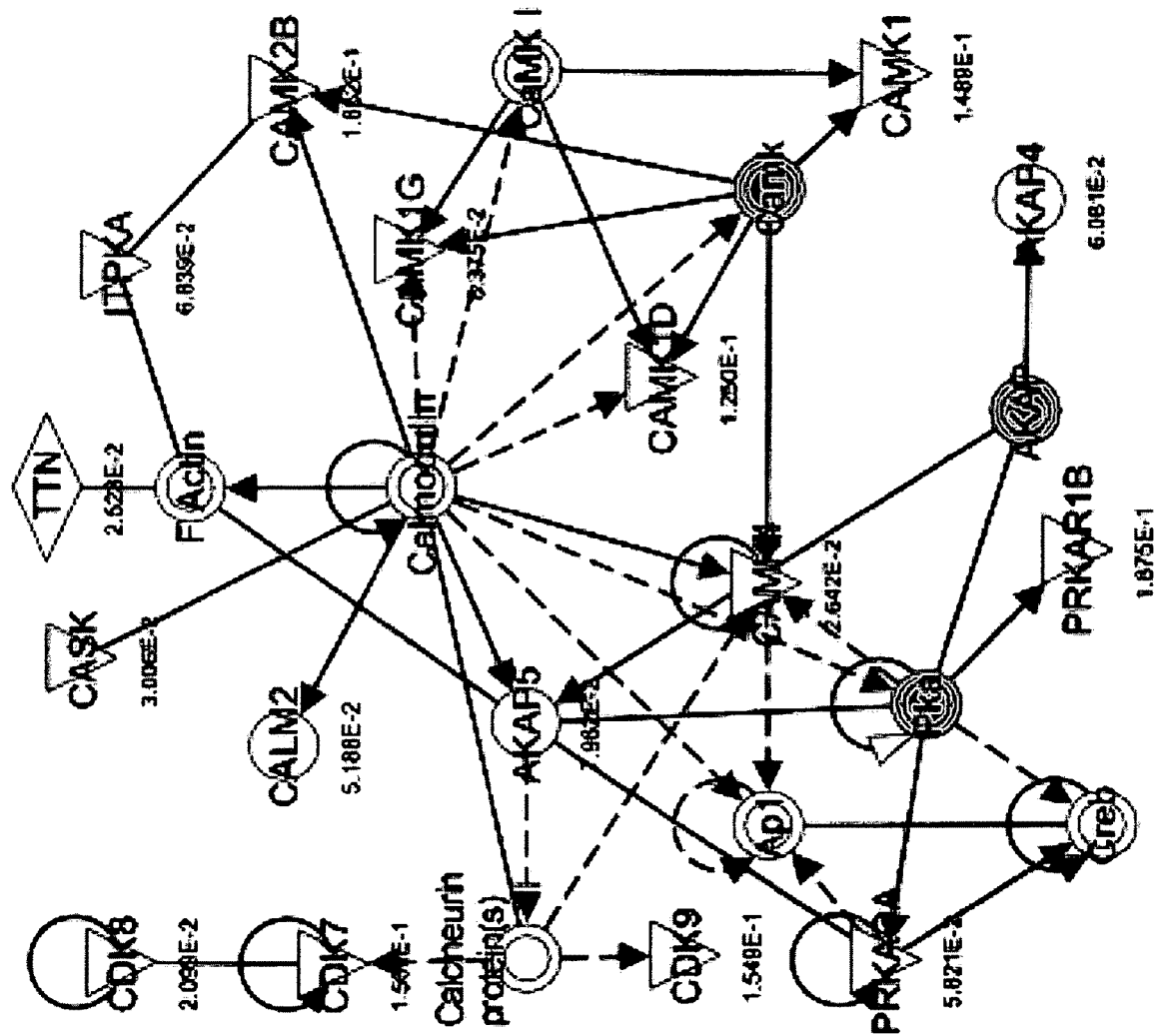

INHIBITION OF FILOVIRUS ENTRY INTO CELLS AND USES THEREOF

CROSS-REFERENCE TO RELATED APPLICATIONS

This continuation-in-part application filed Dec. 21, 2009 and assigned U.S. Ser. No 12/653,916, claims benefit of priority under 35 U.S.C. §120 of international application PCT/US2008/007747, filed Jun. 20, 2008, which claims benefit of priority under 35 U.S.C. §119(e) of provisional U.S. Ser. No. 60/936,426, filed Jun. 20, 2007, the entirety of both of which are hereby incorporated by reference.

This invention was made with government support under National Institute of Allergy and Infectious Diseases (NIAID) Grant No. U54AI057156, awarded by the National Institutes of Health. The government has certain rights in this invention.

BACKGROUND OF THE INVENTION

1. Field of the Invention

The present invention relates to the field of virology. In general, the present invention discloses method(s) of treating infection by members of the filovirus family of viruses by directly inhibiting virus entry into the cells or by preventing envelope protein induced toxicity. More specifically, the present invention discloses methods of treating infection by filovirus such as Ebola virus, Marburg virus and related viruses by blocking the PI3 kinase signaling pathway or the calcium-associated signaling pathway.

2. Description of the Related Art

Ebola virus is a member of the family Filoviridae and causes severe hemorrhagic fevers in humans and nonhuman primates. It is an emerging virus and outbreaks have been reported periodically at 2-10 year intervals since its initial identification in 1976. It is a NIH category A agent and is one of the most widely publicized human viruses. Most outbreaks have occurred in isolated communities in Africa and so have been effectively contained. Release into a large city community would likely have severe consequences not only for those infected but as a result of mass panic and major economic disruption. For these reasons Ebola virus remains one of the most highly effective terrorist bioweapon threats.

In the wild, infections initiate from contact of people with dead or dying virus-infected forest animals such as chimpanzees, forest antelope and porcupines that have been regularly found on the rainforest floor in affected areas (World Health Organization, 2004). However, these are dead-end hosts and the primary animal reservoir remains unknown.

The Ebola virus genus includes four subtypes: Zaire, Sudan, Ivory Coast and Reston. The Zaire strain is the most often associated with outbreaks with very high mortality rates, on average between 80 to 90% (Sadek et al., 1995; Peters, 1996, Peters and LeDuc, 1999; Feldman et al., 1993; Baize et al., 1999; Fisher-Hoch and McCormick, 1999). Virus is spread by contact with blood or body fluids from infected individuals or animals and is highly infectious. The final stages of Ebola virus infection are characterized by fever, hemorrhage, hypotensive shock with an apparent dependence on the reticuloendothelial and mononuclear phagocytic cell systems (Peters and LeDuc, 1999; Baskerville et al., 1978; Baskerville et al., 1985; Feldmann et al., 1996; Schnittler and Feldmann, 1999).

Apart from palliative treatment, there is no effective treatment for an Ebola virus infection. Some success has been found using monoclonal antibodies against envelope proteins and nucleoproteins or using passive transfer of immune serum from convalescent patients (Mupapa et al., 1999; Xu et al., 1998) but this is not practical in the situation of a virus outbreak. Patients that survive typically have more rapid Ebola virus-specific humoral and cellular responses than those that die. Therefore delaying virus spread would give a greater opportunity for the immune system to mount an effective anti-viral response. Then drugs that can prevent or slow an ongoing infection would likely be effective in treatment.

Previous research has suggested that mononuclear phagocytic cells and endothelial cells are sites of Ebola virus replication early in infection although evidence of replication has been observed in many tissues including the liver, spleen and lymph nodes (Connolly et al., 1999; Geisbert et al., 2000; Nabel, 1999; Schnittler et al., 1993; Yang et al., 1998). The pantropic nature of Ebola virus infection suggests a role for monocytes in disseminating the virus to distant sites (Schnittler and Feldmann, 1999; Schnittler and Feldmann, 1998; Stroher et al., 2001). It has been hypothesized that cytokines released from infected mononuclear cells contribute highly to the hypotensive shock and cell damage seen during the later course of infection (Schnittler and Feldmann, 1999; Stroher et al., 2001). Apoptosis is also seen in endothelial cells from fatally infected patients (Baize et al., 1999). There are probably numerous factors involved in the effects seen during Ebola virus infections including virus induced cytokine production that alters vascular permeability, as well as other yet to be identified factors. Identification of these factors is important for the discovery of drugs that can prevent and treat infection and is a major goal of this proposal.

The Ebola virus envelope glycoprotein (GP) determines the cell binding and entry properties of the virus. Ebola virus glycoprotein contains both the receptor-binding domain and fusion mechanism of the virus and is the primary target of a neutralizing antibody response. It is the first virus protein that makes contact with cells and may induce cell-signaling pathways that allow establishment of infection. Ebola virus glycoprotein has also been identified as a major viral determinant of vascular cell cytotoxicity, permeability and injury (Yang et al., 2000). When Ebola virus glycoprotein was expressed at levels comparable to those seen in an in vivo infection, cell death resulted in a variety of cell types. Treatment of cells with Ebola virus envelope protein also resulted in rounding and detachment in culture (Simmons e al., 2002). In rapid entry assays, it was observed that Ebola virus takes a long time (4 h) to penetrate cells compared to other viruses like Murine leukemia virus (20 min) or Vesicular stomatitis virus. These observations suggest that Ebola virus primes or triggers the cell for entry to take place. While it is unlikely that Ebola virus glycoprotein cytotoxicity is solely responsible for the pantropic destruction seen in Ebola virus-induced hemorrhagic fever, this protein is still a major and accessible virulence factor that requires further study.

Thus, prior art is deficient in methods to treat individuals infected with filoviruses. The present invention fulfills this long-standing need and desire in the art.

SUMMARY OF THE INVENTION

In one embodiment of the present invention, there is provided a method of inhibiting entry of a filovirus into a cell. This method comprises contacting the cell with an agent that blocks activity of PI3 kinase signaling pathway protein(s) or calcium-associated signaling pathway protein(s), thereby inhibiting the entry of the filovirus into the cell.

In another embodiment of the present invention, there is provided a method of inhibiting entry of a filovirus into a cell.

Such a method comprises contacting the cell with an agent that downregulates expression of a gene(s) encoding PI3 kinase signaling pathway protein(s) or of a gene(s) encoding calcium-associated signaling pathway protein(s), thereby inhibiting the entry of the filovirus into the cell.

In yet another embodiment of the present invention, there is provided a method of treating an individual infected with a filovirus. This method comprises administering pharmacologically effective amounts of an agent that inhibits activity of the PI3 kinase signaling protein(s) or calcium associated signaling pathway protein(s), thereby treating the individual infected with the filovirus.

In still yet another embodiment of the present invention, there is provided a method of treating an individual infected with a filovirus. Such a method comprises administering pharmacologically effective amounts of an agent that downregulates the expression of gene(s) encoding PI3 kinase signaling pathway protein(s) or calcium-associated signaling pathway protein(s), where the downregulation of the gene inhibits entry of the filovirus into the cells of the individual, thereby treating the individual infected with the filovirus.

In another embodiment of the present invention, there is provided a method of identifying compounds useful in the treatment of infection caused by a filovirus. This method comprises contacting a cell infected with the filovirus with the compound and determining the levels of PI3 kinase signaling pathway protein(s) or calcium associated signaling pathway protein(s), gene(s) encoding said proteins or a combination thereof in the presence and absence of said compound. The levels of the protein(s), the gene(s) encoding the protein(s), or a combination thereof in the presence of the compound are compared with the levels of the protein(s), the gene(s) encoding the protein(s) or a combination thereof in the absence of the compound, where a decrease in the levels of the protein(s), gene(s) encoding the protein(s) or a combination thereof in the presence of the compound is indicative that the compound is useful in the treatment of infection caused by the filovirus.

BRIEF DESCRIPTION OF THE DRAWINGS

FIGS. 1A-1C show validation of luciferase virus entry assay. FIG. 1A shows that entry of Ebola virus GP pseudotype occurs with slow kinetics. Luc-containing Ebola virus (open circle) and VSV (solid circle) GP pseudotypes were incubated with HEK293 cells at room temperature. After 10 mins, cells were washed to remove unbound virus and incubated at 37° C. At indicated time intervals, aliquots of cells were withdrawn and luciferase entry assay performed. For each virus, luciferase activity at different time points was normalized to the maximum luciferase activity for that virus. Each data point represents mean±range of 2 independent experiments. FIG. 1B shows that anti-Ebola virus neutralizing antibody specifically inhibits entry of Ebola virus GP pseudotype. Luciferase entry assay was performed using Ebola virus (open bars) or VSV (solid bars) GP pseudotype and HEK293 cells in the presence of anti-Ebola virus neutralizing antibody (KZ52) or a non-specific antibody (control). Data were normalized to luciferase activity in cells incubated with respective untreated virus. Each data point represents mean±s.d. of 3 independent experiments. FIG. 1C shows that entry of Ebola GP pseudotype is sensitive to inhibitors of endosomal acidification. Luciferase entry assay was performed using Ebola virus, VSV or Fr-MLV GP pseudotype and target cells (HEK293 for VSV and Ebola virus or 293-CAT-1 for Fr-MLV) in the presence of either 20 mM ammonium chloride (open bars) or 50 nM bafilomycin A1 (solid bars). Data were normalized to luciferase activity for untreated cells. Each data point represents mean±s.d. of 3 independent experiments.

FIG. 2A shows the impact of each single siRNA was plotted for the 720 targeted genes as a function of fold-increase in standard deviation over that seen for the negative control non-targeting siRNA (neg 1 and neg 2). Positive controls targeting kif11 and firefly luciferase (fluc) are also indicated. The fluc siRNA suppressed the infection reporter gene encoded by the pseudotyped virus. 15 replicates of each control are shown. For the siRNA that were part of the screen, circles, squares and diamonds indicate distinct siRNA targeting each gene. The cut-off of significance is indicated by the dashed line and corresponds to three times the standard deviation of the control signals. FIG. 2B shows RSA ranking of siRNA hits. All siRNA that suppressed or elevated infection of EBOV envelope protein pseudotyped virus were evaluated using the RSA algorithm that is specifically designed to analyze siRNA screening data from screens using multiple siRNA targeting each gene. Probability scores assigned for each gene are shown. Scores of 10 indicate the gene product was not classified as a potential hit. The threshold used for the network analysis is indicated by the dashed line. All scores below this line were used.

FIG. 3A-3C identified gene product networks impacting infection by the EBOV pseudotyped virus. Three distinct kinase network types were identified using the Ingenuity Pathway Analysis software. These were MAP kinase (MAPK, FIG. 3A), PI3 kinase (PI3K, FIG. 3B) and calcium/calmodulin dependent kinase ($Ca^{2+}$/CALM, FIG. 3C) dependent networks. Genes or gene products are represented by inverted triangles and circles. Lines connecting symbols represent known interactions in the Ingenuity database. Shaded symbols indicate siRNA that were indicated as hits using the RSA algorithm. Numbers below each symbol indicate assigned RSA probability values.

FIG. 4A shows that wortmannin, but not U0126 inhibits entry of Ebola virus. U0216 is an inhibitor of a PI3K independent pathway, thus showing that PI3K inhibition is specific. Entry assays were performed using VSV (solid bars) or Ebola virus (open bars) GP pseudotype and HEK293 cells treated with wortmannin (0.1 µM) or U0126 (15 µM). Data were normalized to luciferase activity in DMSO (vehicle)-treated cells. Each data point represents mean±s.d. of 3 independent experiments. FIG. 4B shows that PI3K inhibitor LY294002 and Akt-1 inhibitor inhibit Ebola virus entry. Entry assays were performed using VSV (solid bars) or Ebola virus (open bars) GP pseudotype and HEK293 cells were treated with LY294002 (50 µM) or Akt-1 inhibitor (1.0 µM). Data were normalized to luciferase activity in DMSO (vehicle)-treated cells. Each data point represents mean±s.d. of 3 independent experiments. FIG. 4C shows that dominant negative mutant of the regulatory subunit of PI3k reduces Ebola virus entry. HEK293 cells were transfected with either pcDNA3 (empty vector) or a pcDNA3 encoding Δp85α. Entry assays were performed 36 h after transfection using VSV (solid bars) or Ebola (open bars) GP pseudotypes. Data were normalized to luciferase activity in untransfected cells. Each data point represents mean±s.d. of 2 independent experiments. FIG. 4D shows that inhibitors of PI3K-Akt-1 pathway do not affect binding of Ebola virus to the target cells. HEK293 cells were pre-treated with LY294002 (50 µM) or Akt-1 inhibitor (1.0 µM) for 1 h at 37° C., followed by incubation with Ebola env pseudotyped virus for 10 min at room temperature. Cells were then washed to remove unbound virus, resuspended in luciferase assay buffer containing triton X-100 detergent and luciferase activity measured. Data were normalized to luciferase activity in vehicle-treated samples. Each data point represents mean±s.d. of 2 independent experiments.

FIG. 5 shows that Ebola GP pseudotyped virus promotes Akt-1 phosphorylation. Serum starved HEK293 cells were incubated with serum-free medium, Ebola GP pseudotyped virus or medium containing 10% fetal bovine serum, as indicated. After 1 h, cells were lysed and phosphorylated Akt-1 was detected by Western blot (p-Akt-1, upper panel). Subsequently, the same membrane was stripped and reprobed for total Akt-1 (lower panel).

FIGS. 6A-6C show that Rac1 plays a role in Ebola virus entry and serves as a downstream effector of Akt-1 signaling. FIG. 6A shows that inhibitor of Rac1 inhibits Ebola virus entry. Cells were treated with Rac1 inhibitor (100 μM) and entry assays were performed using VSV or Ebola GP virus pseudotypes. Each data point represents mean±s.d. of 3 independent experiments. FIG. 6B shows expression of dominant negative Rac1 results in inhibition of Ebola virus entry. HEK293 cells were transfected with either pcDNA3 (open bars) or pcDNA3 encoding dominant-negative Rac1 (Rac1-T17N, solid bars). Entry assays were performed 36 h later using VSV or Ebola GP pseudotypes. Results are expressed as percent of luciferase activity in untransfected cells. Each data point represents mean±range of 2 independent experiments. FIG. 6C shows that expression of constitutively active Rac1 overcomes the inhibitory effect of Akt-1 inhibitor on Ebola virus entry. HEK293 cells were transfected with either pcDNA3 (open bars) or pcDNA3 encoding constitutively active Rac1 (Rac1-G12V, solid bars). Entry assays were performed 36 h later, in the presence of Akt-1 inhibitor (1.0 μM) using VSV or Ebola virus GP pseudotypes. Results are expressed as percent of luciferase activity in vehicle-treated sample of each representative virus. Each data point represents mean±range of 2 independent experiments.

FIG. 7 is a model depicting role of PI3K in Ebola virus entry. Attachment of Ebola virus to the cell surface receptor (step 1) activates PI3K (step 2) indirectly leading to phosphorylation and activation of Akt-1 (step 3). Activated Akt-1 causes activation of Rac 1, involving GDP to GTP exchange (step 4), which then promotes assembly of the actin cytoskeleton, possibly at the site of viral attachment (step 5), facilitating membrane trafficking, virus endocytosis and/or fusions (steps 6 and 7).

FIG. 8 shows specific inhibition of Ebola entry by siRNA targeting AK7, CAMK2 and DMPK. Cells were transfected with specific siRNA by reverse transfection. After 2 days, (siRNA inhibition peak) cells were challenged with Ebola envelope-pseudotyped viruses carrying a Firefly Luciferase reporter gene. Cells were simultaneously infected with a ecotropic murine leukemia virus envelope (MLV)-pseudotype carrying a Renilla Luciferase reporter gene (both luciferases are measured independently). The MOI for each was less than 0.05 (fewer than ½0 cells infected by each, fewer than ¼00 cells by both). This internally controls for adverse effects of siRNA challenge for each siRNA and allows rapid identification of siRNA that specifically inhibit Ebola virus. The bars indicate change in virus infectivity relative to negative controls.

FIG. 9 shows that CAMK2 plays a role in Ebola virus infection by treatment with the specific CAMK2 inhibitor KN-93. Left: 293 cells were treated with KN-93 or vehicle control (DMSO) and challenged with retrovirus pseudotypes bearing Ebola virus or eMLV (Fr-MLV) envs. Luciferase activity was used to measure infection. Right: 293 cells were treated as described with KN-93 or its inactive homolog KN-92 (both at 10 μM). Cells were infected with either Ebola virus or Venezuelan equine encephalitis virus (VEEV) pseudotyped VSV particles. KN-93 specifically blocked infection with Ebola virus. Infection relative to untreated cells is shown.

FIG. 10 shows cells treated with Tetrandine or Diltiazem at 5 or 10 μM, respectively. They were then infected with virus-like particles bearing Ebola virus (solid bars) or Venezuelan equine encephalitis virus (open bars) envs. Infection was measured by counting GFP-expressing cells.

FIGS. 11A-11B validate usage of drugs for treatment of infection of the live virus. FIG. 11A shows effect of indicated calmodulin inhibitor (Phenoxybenzamine hydrochloride (Pheno)) and L-channel blocking drugs (Verapamil (Verap), Nimodopine (Nimod) and Methoxyverapamil (MethV)) on Ebola virus entry into cells. Drugs were tested on virus-like particles bearing Ebola (Eb) or Venezuelan equine encephalitis virus envelope proteins. FIG. 11B shows inhibition of infection of live Ebola Zaire virus by inhibitors of PI3K (LY294002) and the calcium blocker (methoxy-verampil). Vero E6 cells were infected with either live Vesicular stomatitis virus (Indiana strain; solid bars) or live Ebola virus (Zaire strain; open bars) after being treated either at 50 and 100 uM, respectively. After 6 hours, the drugs were removed and new medium added. Cells were cultivated for 2 or 10 days for Vesicular Stomatits virus or Ebola virus, respectively and plaques were counted. Plaque numbers were normalized to DMSO (drug vehicle) treated controls.

Figure 12:
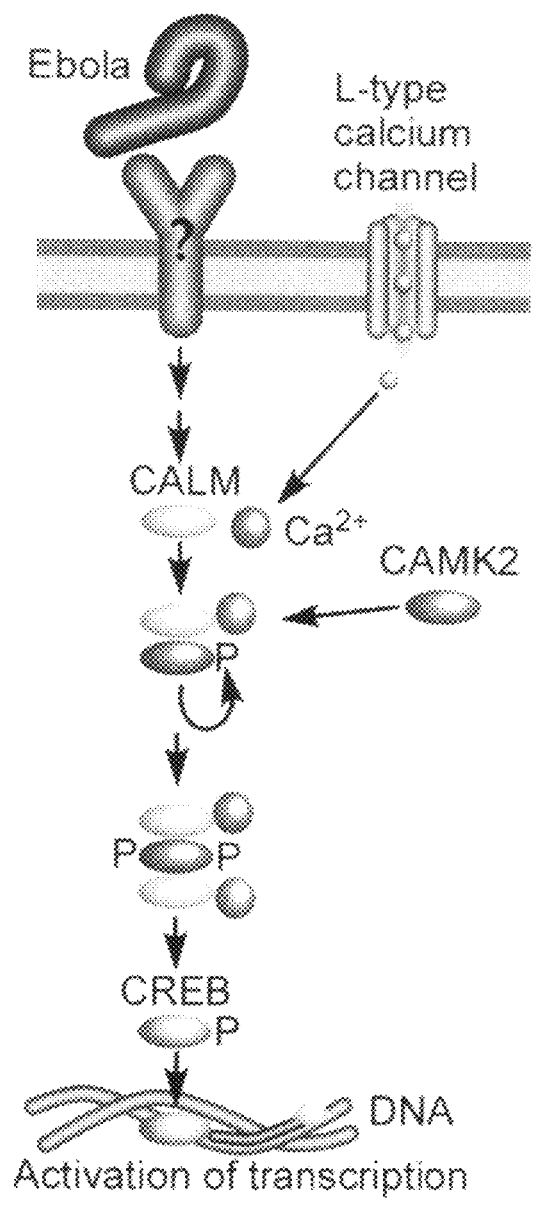

FIG. 12 shows CREB activation pathway of transcription. It is proposed that Ebola virus binding to its (as yet unidentified) receptor activates a calcium influx into the cell which in turn activates calmodulin (CALM) and CAMK2 which trigger transcriptional activation through CREB. This is key for Ebola virus infection.

FIG. 13A shows EBOV pseudotyped lentivirus was added in the presence of each drug and then incubated with virus for 6 h. Both drug and unbound virus were then removed and cells were assayed for infection 40 h later by measuring expression of a reporter gene (firefly luciferase). The average of 4 replicates±st. dev. is shown. FIG. 13B demonstrates that drug activity was not against the lentivirus core, a vesicular stomatitis virus core was used to make additional pseudotyped viruses. Aside from EBOV pseudotyped particles (open bars), an additional pseudotype was made, using the envelope proteins of VEEV (solid bars). Each drug was tested at 100 mM. The average of two replicates±st. dev. is shown.

DETAILED DESCRIPTION OF THE INVENTION

Figure 2A:
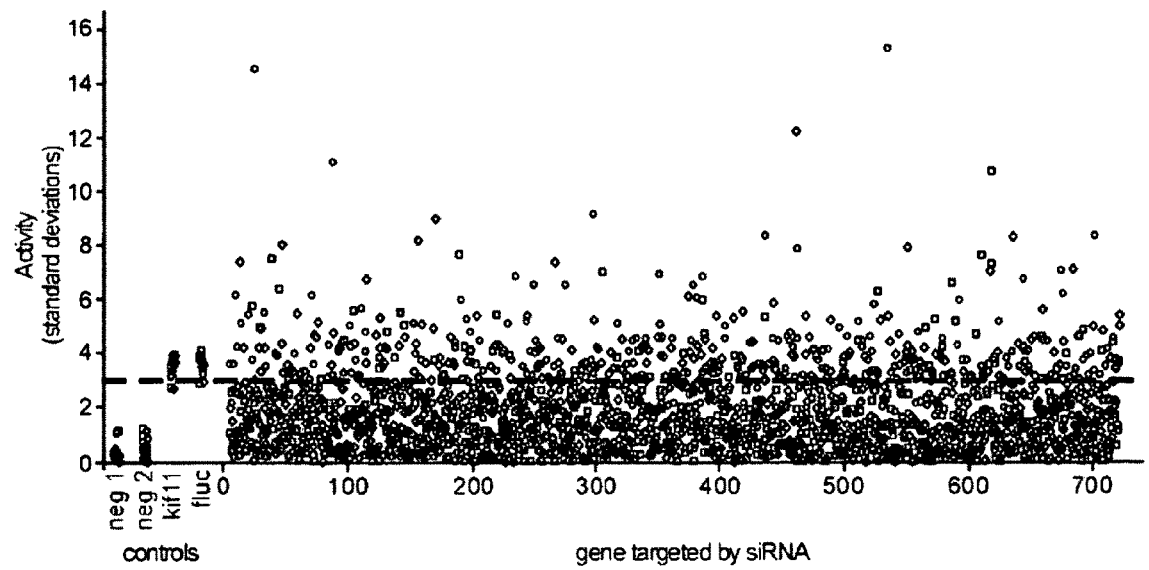
FIG. 2A-2B shows the distribution of effects of siRNA on infection of EBOV pseudotyped viruses.

The present invention is drawn to treatment of individuals infected with filoviruses, which include but is not limited to Ebola virus and Marburg virus. Specifically, the present invention is drawn to treating such infections by directly inhibiting virus entry into cells or by preventing envelope protein induced toxicity. The envelope protein (env or GP) define the majority of cell tropism for enveloped viruses by determining receptor specificity and thereby, entry route into the cells. Virus GP pseudotypes are virus-like particles that bear the GP proteins of one virus over the core of another. They function as good proxies to study virus entry in relative safety. Additionally, they are accepted by most in the field to adopt the entry mechanism and pathway. FIG. 11 demonstrates that the information gained using such pseudotypes corresponds to that attained with live virus.

Briefly, it is demonstrated herein that inhibition of protein activities in the PI3 kinase pathway (PI3K, Akt or Rac-1) effectively blocked entry of Ebola envelope protein (GP) bearing virus particles. PI3K and Akt make up a key cell signaling pathway that become dysfunctional in many cancers. Also demonstrated herein is that inhibition of calmodulin, CAMK2 enzyme or inhibition of $Ca^{2+}$ channels, effectively blocked entry of Ebola envelope protein (envs) bearing virus particles. Each of these proteins represents a link in the chain of a major cellular calcium-associated signaling pathway. Calcium signaling has been shown to be key in triggering numerous responses in cells including gene transcription. It is a key cell signaling pathway that becomes dysfunctional in many chronic diseases including high blood pressure and Alzheimer's disease.

A rapid entry assay was used herein to determine the effect of inhibition of PI3 kinase pathway on the entry of the filovirus such as Ebola virus. The PI3 kinase pathway was inhibited using siRNA, LY294002, Wortmannin or Akt-1 inhibitor. Such inhibition resulted in inhibition of entry of Ebola virus in the cells but not the binding of the Ebola virus to the target cells. Thus, it is concluded herein that inhibition of PI3K, Akt or Rac-1 blocks the Ebola virus infection at the point of virus entry. This is because Ebola virus entry likely requires cytoskeleton rearrangement in the cell that is stimulated by activation of PI3K and Akt. This pathway has been shown to be involved in cancer formation. Hence, drugs that treat cancer by suppressing the PI3 kinase pathway should function as effective cures for infections caused by filovirus such as Ebola virus. It is also contemplated that most filoviruses will be affected by these drugs in the same manner as the Ebola virus since they use the same pathway for infection. Additionally, since this treatment does not work for murine leukemia viruses or VSV, it is presumed that such a treatment is limited to filoviruses.

Furthermore, inhibition of CAMK2 using siRNA targeting CAMK2 and a CAMK2 inhibitor such as KN-93 blocked entry of Ebola virus into cells. Additionally, since calmodulin acts to recruit and trigger CAMK2 by binding the released calcium, calmodulin inhibiting drugs such as phenoxybenzamine, W7 and trifluorperazine were used to treat cells infected with Ebola virus. It was observed that these drugs inhibited Ebola virus infection. Further, treatment of cells with calcium channel blocking drugs such as tetrandine and diltiazem specifically blocked Ebola virus infection. Of the numerous calcium channel drugs specific for 4 classes of channels (L, N, P/Q and R) that were screened, L-channel blocking drugs such as Verapamil and its derivative methoxyverapamil, Nimodopine and other dihydropyridines were found to be effective against Ebola virus entry. Since transient treatment with these drugs is sufficient to irreversibly block Ebola virus entry, it is contemplated that a short term usage of these drugs should be effective in preventing Ebola virus infection and spread.

Thus, it is concluded that inhibition of $Ca^{2+}$ channels, calmodulin or CaMK2 blocks Ebola virus infection at the point of virus entry. This is because Ebola virus entry likely requires transcriptional activation of the cell and synthesis of some factor, possibly through activation of the nuclear transcription factor, CREB. This pathway has been shown to be involved in transmitting calcium-based signals to the cell nucleus by hormones and other stimuli. Aside from the drugs tested herein, it is contemplated that any calcium L-channel blocking drug will work similarly. Additionally, most filoviruses will be affected by these drugs as they use the same pathway for infection. Since the treatment does not work for eMLV or VEEV, it is presumed that the treatment is specific for filoviruses. It is also likely that the calcium influx induced by Ebola virus particles is responsible for the increase in vascular permeability syndrome (profuse internal vascular bleeding and leakage of blood fluids from blood vessels, etc) seen during infection that ultimately kills patients. If so, then treatment with calcium channel blockers would also reduce this cytotoxicity, treat Ebola virus associated disease symptoms and could potentially cure the patient.

The present invention is directed to a method of inhibiting entry of a filovirus into a cell, comprising: contacting the cell with an agent that blocks activity of PI3 kinase signaling pathway proteins or calcium-associated signaling pathway protein, thereby inhibiting the entry of the filovirus into the cell. Representative examples of the PI3 kinase signaling pathway protein may include but is not limited to PI3 kinase, Akt, Rac-1 or a combination thereof. Representative examples of such an agent may include but is not limited to Wortmannin, LY294002, an Akt-1 inhibitor, a Rac-1 inhibitor or a dominant negative Rac-1. Alternatively, representative examples of the calcium-associated pathway protein may include but is not limited to calmodulin, CAMK2 enzyme or $Ca^{2+}$ channels. Representative examples of such an agent may include but is not limited to KN-93, Tetrandine, Diltiazem or a L-type channel blocker. Further, representative examples of the L-type channel blocker may include but is not limited to verapamil, methoxyverapamil or other dihydropyridine. Furthermore, representative examples of the filovirus may include but is not limited to an Ebola virus or a Marburg virus.

The present invention is also directed to a method of inhibiting entry of a filovirus into a cell, comprising: contacting the cell with an agent that downregulates expression of a gene(s) encoding the PI3 kinase signaling pathway protein(s) or a gene(s) encoding calcium-associated signaling pathway protein(s), thereby inhibiting the entry of the filovirus into the cell. Representative examples of gene(s) downregulated by such an agent may include but is not limited to the gene(s) that encodes PI3 kinase, Akt, Rac-1 or CAMK2. Additionally, representative examples of the filovirus may include but is not limited to an Ebola virus or a Marburg virus. Furthermore, examples of the agent that can be used in such a method may include but is not limited to a siRNA, a peptide nucleic acid, an inorganic chemical compound, an organic chemical compound or a polypeptide.

The present invention is further directed to a method of treating an individual infected with a filovirus, comprising: administering pharmacologically effective amounts of an agent that inhibits the activity of the PI3 kinase pathway proteins or calcium-associated signaling pathway thereby treating the individual infected with the filovirus. Such an inhibition may block the entry of the filovirus into cells of the individual. Further, representative examples of the PI3 kinase signaling pathway proteins may include but is not limited to PI3 kinase, Akt, Rac-1 or a combination thereof and those of the calcium-associated signaling pathway may include but is not limited to calmodulin, CAMK2 enzyme or $Ca^{2+}$ channels. Representative examples of such agents may include but is not limited to Wortmannin, LY294002, an Akt-1 inhibitor, a Rac-1 inhibitor, a dominant negative Rac-1, KN-93, Tetrandine, Diltiazem, dihydropyridine or a L-type channel blocker. Additionally, representative examples of the L-type channel blocker may include but is not limited to Verapamil or methoxyverapamil. Representative examples of the filovirus may include but is not limited to an Ebola virus or a Marburg virus.

The present invention is still further directed to a method of treating an individual infected with a filovirus, comprising: administering pharmacologically effective amounts of an agent that downregulates the expression of gene(s) encoding PI3 kinase signaling pathway protein(s) or calcium-associated signaling pathway protein(s), where the downregulation of the expression of the gene(s) inhibits the entry of the filovirus into cells of the individual, thereby treating the individual infected with the filovirus. Examples of the agent useful in such a method may include but is not limited to a siRNA, a peptide nucleic acid, an inorganic chemical compound, an organic chemical compound or a polypeptide. Additionally, examples of the genes whose expression is downregulated by the agent may include but is not limited to genes encoding PI3 kinase, Akt, Rac-1 calmodulin, CAMK2 or L-type calcium channels. Examples of the filovirus may include but is not limited to an Ebola virus or a Marburg virus.

The present invention is also directed to a method of identifying compounds useful in treatment of infection caused by a filovirus, comprising: contacting a cell infected with the filovirus with the compound; determining the levels of PI3 kinase signaling pathway protein(s) or calcium associated signaling pathway protein(s), gene(s) encoding the proteins or a combination thereof in the presence and absence of the compound; and comparing the levels of the protein(s), the gene(s) encoding the protein(s), or a combination thereof in the presence of the compound with the levels of the protein(s), the gene(s) encoding the protein(s) or a combination thereof in the absence of the compound, where a decrease in the levels of the protein(s), the gene(s) encoding the protein(s) or a combination thereof in the presence of the compound is indicative that the compound is useful in the treatment of infection caused by the filovirus. This method may further comprise: performing viral entry assay to determine the ability of the compound to inhibit entry of the filovirus in the cell. Examples of the PI3 kinase signaling pathway protein may include but are not limited to PI3 kinase, Akt or Rac-1 and those of the calcium-associated signaling pathway protein may include but is not limited to calmodulin, CAMK2 enzyme or $Ca^{2+}$ channels. Representative examples of the filovirus may include but are not limited to an Ebola virus or a Marburg virus.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term "PI3K" means PI3 Kinase. Whereas the term "PI3 kinase signaling pathway" means those proteins that form part of a signaling cascade including PI3 kinase. As used herein, the term "GP" means the envelope glycoprotein of a virus. As used herein, the term "h" means hour.

As used herein, the term "contacting" refers to any suitable method of bringing the agent described herein into contact with a virally infected cell. In vitro or ex vivo this is achieved by exposing the infected cell to the agent in a suitable medium. For in vivo applications, any known method of administration is suitable as described herein.

The agents described herein can be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The agents described herein may be administered independently one or more times to achieve, maintain or improve upon a therapeutic effect. It is well within the skill of an artisan to determine dosage or whether a suitable dosage of the agents described herein comprises a single administered dose or multiple administered doses. An appropriate dosage depends on the subject's health, inhibition of the PI3 kinase or calcium-associated signaling pathways and blockage of viral entry into the cells, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Materials and Methods

All chemicals were Ultragrade from Sigma (St. Louis, Mo.) unless stated otherwise. Dharmafect Cell Culture Reagent (DCCR) and DharmaFECT 1 transfection reagent used for siRNA transfection were from Dharmacon (Lafayette, Colo.).

Cells were maintained in a humidified air-5% $CO_2$ atmosphere incubator at 37° C. 293 FT cells (Invitrogen, Carlsblad, Calif.) were used to express envelope proteins by plasmid transfection. Screens were performed using HEK293 cells and were grown in DMEM (Invitrogen, Carlsblad, Calif.) supplemented with 10% fetal bovine serum (Gemini Bioproducts, West Sacramento, Calif.). Vero-E6 cells were used for verification of drug activities on wild type virus and were cultured as for HEK293 cells.

Cultivation of Wild Type Ebov and Determination of Virus Titer

EBOV, Zaire strain, was cultivated on Vero-E6 cells by infection at an MOI of 0.1. Culture supernatants were collected after 10 d and clarified by centrifugation at 2000×g for 15 min. Virus concentration was determined by titration on Vero-E6 cells. Cells were incubated with virus for 1 h and then overlaid with 0.8% tragacanth gum in DMEM/4% FBS. 10 d post-infection cells were fixed with 2% formalin and stained with crystal violet to count plaques. All experiments with EBOV were performed under biosafety level 4 conditions in the Robert E. Shope BSL-4 Laboratory, UTMB.

Production of Envelope Protein Pseudotyped Lentiviruses

Pseudotyped lentiviruses were produced following published methods [Kolokoltsov et al. 2005]. Virus envelope protein pseudotyped lentiviruses (LV) were prepared for use in siRNA screens and as controls in drug treatment experiments. Pseudotypes were made bearing the envelope EBOV Zaire strain. For screening purposes, the LV pseudotype encoded firefly luciferase as the reporter of infection. Pseudotyped virus was assembled by transfecting 293 FT cells (Invitrogen) with plasmids encoding HIV LV core structural proteins (pLP1), HIV Rev (pLP2) together with plasmids encoding the firefly luciferase reporter gene (pLENTI6-fluc) and the envelope protein of the Zaire strain of EBOV (pEBOVenv). The EBOV envelope expression construct was supplied by Dr. Sanchez (CDC). The firefly luciferase reporter construct, pLENTI6-fluc, was made by inserting a codon optimized firefly luciferase gene between BamHI and XhoI sites of the pLENTI6 plasmid (Invitrogen). Transfection was done by calcium phosphate [Chen and Okayama 1987]. After 2 d, culture supernatants were collected, filtered through a 0.45 mm filter to remove cell debris, and the filtered virus was used immediately or stored frozen at −80° C.

The titer of the pseudotyped virus was determined by limiting dilution on HEK293 cells. The concentration of virus was then optimized to yield 20-50,000 cps per 10 ml of virus culture supernatant added per well of a 96-well plate. The expression of luciferase was detected 36 h post-infection using a Veritas 96-well plate reading luminometer. Assays were performed in white walled 96-well Costar tissue culture plates (Corning, Lowell, Mass.). From previous work, approximately 100 cps corresponded to 1 colony forming units of virus. This set the MOI for infection to 0.05 per well.

Production of Envelope Protein Pseudotyped Vesicular Stomatitis Viruses

Vesicular stomatitis virus core pseudotyped virus was made according to described methods [Matsuura et al. 2001]. HEK293 cells were transfected with plasmids encoding EBOV (described above) or VEEV envelope protein [Kolokoltsov et al. 2005]. After 24 h, the cells were infected with a GFP-encoding VSV parent stock virus that was defective for VSV-G expression (provided by Dr. M. Whitt, University of Tennessee, Memphis) and progeny pseudotyped virus harvested after a further 24 h. The titer of the pseudotyped virus was determined by counting GFP-expressing infected cells, 18 h post infection, using an epifluorescence microscope.

siRNA Library Screening and Analysis

The siRNA library used was a subset of the druggable genome library (Ambion, Austin, Tex.) comprising siRNA targeting kinase and phosphorylase genes. A total of 720 distinct genes were targeted using 3 independent siRNA for each gene. Each siRNA was tested independently in separate wells.

The method used was described [Kolokoltsov et al. 2007]. All transfections were performed in 96-well format. The siRNA was dissolved in 25 ml of 1.6% (v/v) stock of DharmaFECT 1 transfection reagent in DCCR (Dharmacon, Calif.) and incubated for 30 min. Then $0.5 \times 10^4$ HEK293 cells in 100 ml medium were added and incubated for 24 h. The final concentration of pooled siRNA per well was 40 nM. This amount was sufficient to reduce the expression of recombinant firefly luciferase by 95% [Kolokoltsov et al. 2007]. Also, this amount was shown to effectively reduce expression of numerous endogenous genes by at least 5-fold, as determined by Western blot [Kolokoltsov et al. 2007].

For screening purposes, 48 h after transfection with siRNA, pseudotyped virus was added to HEK293 cells at an MOI of 0.05. Firefly luciferase expression was measured at 36 h post-infection using Dual-glo reagent (Promega, Madison, Wis.) in a Veritas plate reader (Turner Biosystems, CA). Controls used in the assays were use of transfection reagent alone, and two non-targeting siRNA (Ambion, Tex.). Two other siRNA served as positive controls and indicators of transfection efficacy and knockdown efficacy. One was against firefly luciferase (Ambion, Tex.) which suppressed expression of pseudotyped virus-encoded firefly luciferase. The second was against kif11 (Ambion, Tex.) which when suppressed, is cytotoxic, suppressing productive infection. In all cases, cell viability was checked by visual inspection using phase contrast microscopy.

Analysis of screening results was performed in two phases. The first phase used a recently reported algorithm, redundant siRNA activity analysis (RSA), that was specifically designed to analyze data from siRNA screens [Konig et al. 2007]. The algorithm takes into account the fact that siRNA targeting the same gene may not be equally effective at inducing a knockdown effect. The importance of a gene in assay outcome is determined by assigning probability values that define the statistical significance of the impact of a set of siRNA targeting one gene that yielded a significant effect on the assay being used. This approach has been shown to be more effective at identifying active siRNA, with higher confirmation rates, in high throughput screens than standard ranking methods [Konig et al. 2007]. For this, the activity of the luciferase infection reporter, in cells transfected with library siRNA, was normalized to the mean of the signals obtained for the negative control siRNA. The negative control siRNA had been performed at least 39 times each for the assay and were distributed throughout the sets of plates. The normalized data was then analyzed using the RSA algorithm implemented in the Perl programming language. Two sets of data were generated. One set analyzed reductions in activity of the infection reporter and the other analyzed increases in the infection signal. Values less than or equal to 0.58, or more than or equal to 1.72 times the mean of the control siRNA were used as the cut-off thresholds respectively. This corresponded to 3 times the average standard deviation of the signals from the control sets.

In the second phase of analysis, the assigned probability values generated by the RSA algorithm and associated gene identifiers were submitted for analysis using the Ingenuity Pathways Analysis software package (Ingenuity Systems, www.ingenuity.com). Each gene identifier was mapped to known networks in the Ingenuity Pathways Knowledge Base. A cutoff value of less than or equal to a probability score of 0.2 was set as the threshold for selection of genes of interest. For canonical pathways, p-values were calculated by the Ingenuity software using Fischer's exact test, which is a measure of the probability that the selected genes are associated with a pathway by chance alone.

Drug Treatments

To confirm involvement of siRNA identified signaling proteins in EBOV entry and infection, cells were challenged with virus in the presence of specific inhibitor drugs. KN-93 inhibits calmodulin kinase 2 (CAMK2). KN-92 is a derivative of KN-93 that has weak affinity for CAMK2 and served as a negative control for off-target activities. LY294002 was used to target phosphatidylinositol-3-kinase (PI3K) and is widely accepted to be specific for PI3K with no appreciable off-target effects at the concentration used. In each case the drugs were dissolved in DMSO to give a 100× concentrated stock solution and were diluted in culture medium immediately before use.

For testing of drugs, both pseudotyped virus and wild type EBOV were used. Cells were prepared similarly for each assay. Cells were seeded to 50% confluency, which is approximately $10^4$ cells for each well of a 96-well plate or $5\times10^5$ cells for each well of a 6-well plate. The plate was incubated at 37° C. for 4 h to allow for cell attachment. For pseudotyped virus, HEK293 cells were used in 96-well plates while Vero cells in 6-well plates were used for wild type EBOV. Each drug was added to the cells 1 h before addition of virus. The medium was then replaced with fresh medium containing drug and virus. Typical infection dosage was at an MOI of 0.005 for wild type EBOV or 0.05 for pseudotyped virus.

For the pseudotyped lentivirus, assays were read after 40 h. The medium was removed and Dual-glo luciferase substrate added (Promega, Madison, Wis.), following the manufacturer's recommendations. The plate was then read using a Veritas luminometer (Turner Biosystems, Sunnyvale, Calif.). For wild type EBOV, cell monolayers were treated as described for determination of virus titer and plaques were counted. For the pseudotyped VSV particles, assays were read at 18 h post infection by counting GFP-expressing cells using an epifluorescence microscope. Statistical analysis, curve fitting and calculation of IC50 values was performed using Graphpad Prism software (GraphPad Prism version 4.00 for Windows, GraphPad Software, San Diego Calif. USA, www.graphpad.com). Data were compared by one way ANOVA with the Tukey-Kramer post test.

Example 2

Inhibition of Filovirus Entry into Cells by Blocking of the PI3 Kinase Pathway

Figures 1A, 1B, 1C:
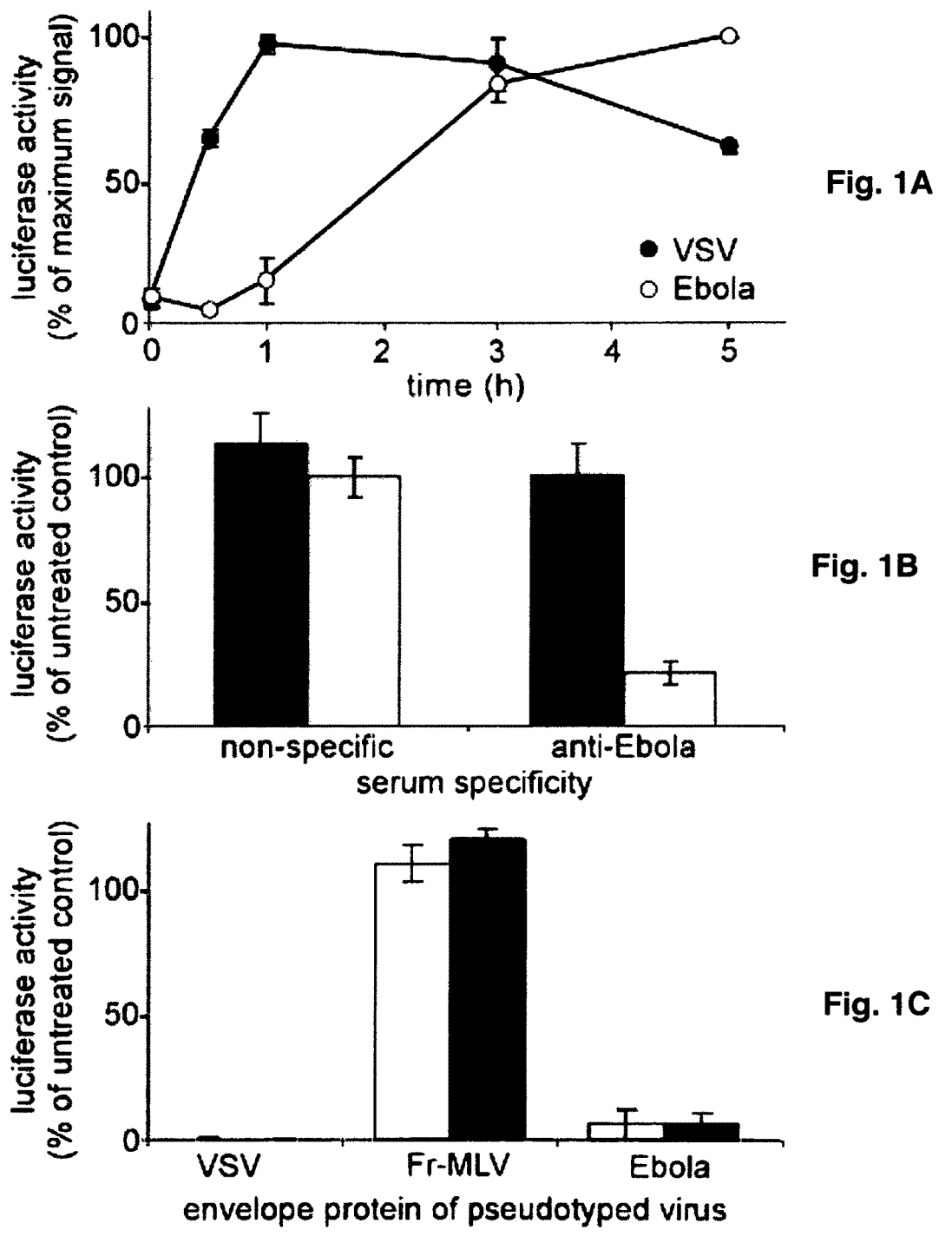

A rapid entry assay developed for Ebola virus pseudotypes was used herein. This is potentially a powerful diagnostic tool (FIG. 1). Briefly, human-derived 293 HEK cells which are generally accepted as good models for study of virus infection of cells in the human body were used herein. Initial work identified the potential role of PI3 Kinase isoforms in Ebola virus infection by performing an siRNA screen by treating cells with siRNA targeting cell kinase genes. The activity of genes important for infection by each virus was identified by comparing cells infected with either Ebola Zaire or ecotropic murine leukemia virus (eMLV) GP pseudotyped viruses. Since eMLV and Ebola virus envs have different receptor specificities and functions, differences between the infection activity of each virus indicated specific genes important for the respective virus. The screen was set up to give readout of infection by two independent viruses. Firefly luciferase (fLuc) and Renilla luciferase (RLuc) were used as reporters of infection for Ebola virus and eMLV pseudotypes respectively. Through this screen PI3Kinase was identified as important for Ebola virus infection but did not influence eMLV.

To identify new potential leads for developing antiviral therapies against EBOV an siRNA library targeting cell kinases and phosphatases, often referred to as the kinome was screened. Both sets of enzymes are important drug targets, as they are active in many aspects of cell function that could impact virus infection. These include receptor-ligand mediated signaling pathways, gene regulation and cell cycle control. They are also often found dysregulated in many chronic diseases such as cancers.

An EBOV envelope protein pseudotyped virus was used for screening. A viral pseudotype is a virus particle that bears the envelope proteins of a virus of interest over the core of another virus, in this case a lentivirus. The pseudotyped virus particle typically adopts the receptor specificity, cell tropism and entry characteristics dictated by the foreign envelope protein. Retroviruses are often used to make pseudotypes as they readily adopt new envelope proteins which can function to give infection by the retrovirus core. Retroviral pseudotypes are also advantageous as they can be made in the absence of the natural envelope proteins and with replication incompetent genomes that are modified to express marker proteins upon infection. Such pseudotyped viruses recapitulate the entry characteristics of the envelope protein donor and EBOV retrovirus pseudotypes have been used to study EBOV infection mechanisms. Most importantly, pseudotyped viruses offer the ability to study the features of a highly pathogenic virus at lower biocontainment and are more amenable to high-throughput screening platforms. Nonetheless, it is still important to validate all findings attained with pseudotyped viruses by testing live virus as well.

Figure 2B:
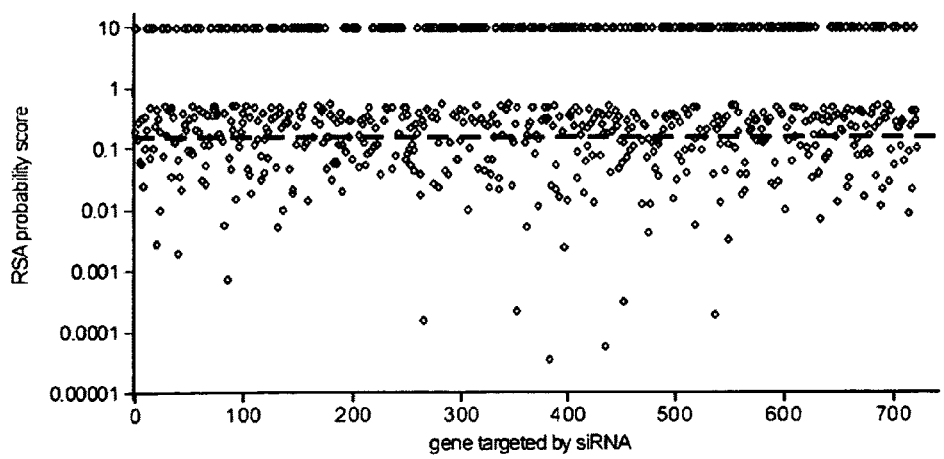

Since three distinct siRNA were screened per gene target, it was important to rank the importance of targets based on the overall impact of each set of siRNA on infection. This is relevant because not all siRNA perform equally well. Simple ranking of siRNA effectiveness based on a single strong effect of one siRNA or the average effect of each does not take this into account. For this, redundant siRNA activity (RSA) analysis was used. This algorithm assigns a probability score (p-value) that indicates the statistical relevance for each gene being important for screening outcome, based on the extent of impact on the assay and the performance of each siRNA targeting the same gene [Konig et al. 2007]. The cut-off threshold used in this analysis was set to 3 times the standard deviation in signals seen in the negative and positive controls (one standard deviation was 14%). Therefore a change of or less than or equal to 0.58 or greater than or equal to 1.72 times the average infection rate seen for controls was used as the threshold for significance. One quarter (26.2%) of the siRNA were defined as potential hits, having a significant impact on pseudotyped virus infection. These siRNA not only inhibited infection but many (45% of the active siRNA) actually increased the infection signal (FIG. 2). The latter may indicate that these siRNA inhibited expression of cell proteins that misdirect virus into non-productive pathways or are part of anti-viral host defense mechanisms.

Figure 3A:
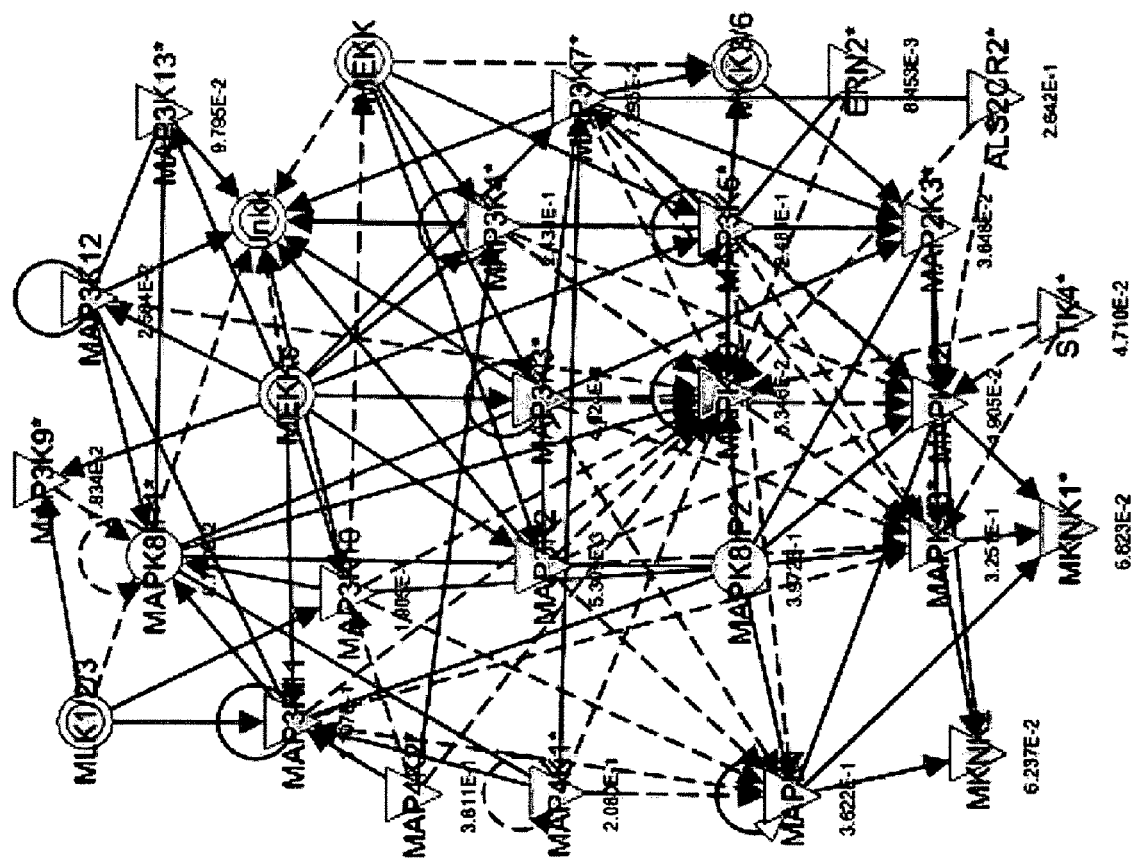
Figure 3B:
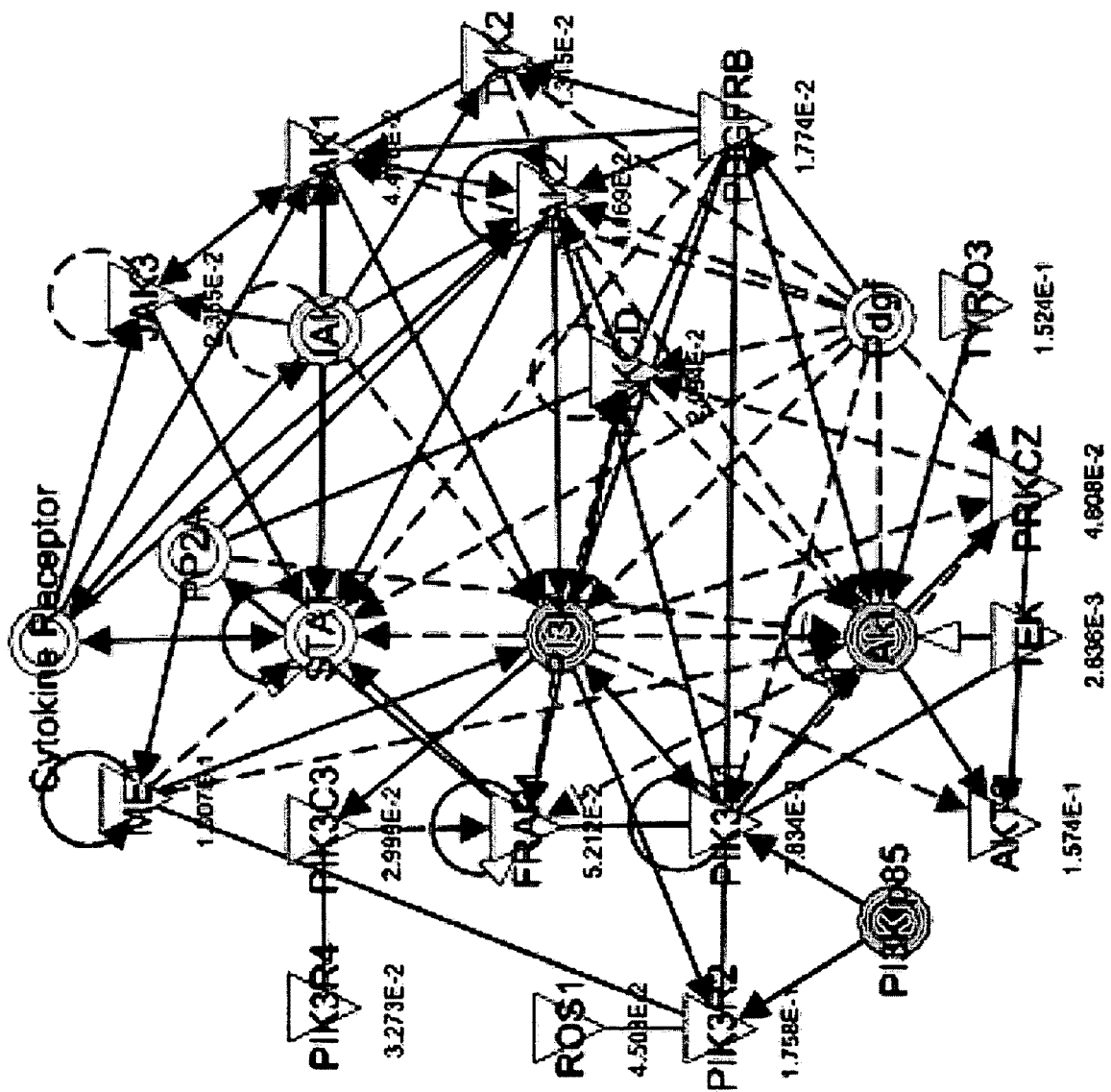
Figure 4A:
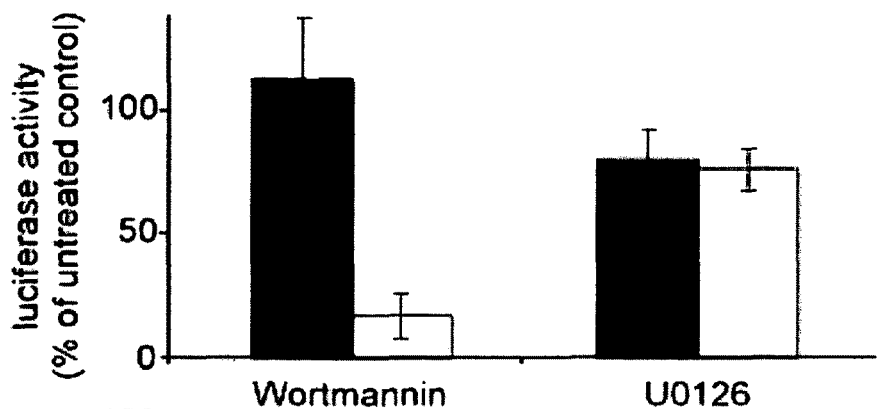
FIGS. 4A-4D show that PI3K-Akt-1 pathway plays a critical role in Ebola virus entry.
Figure 4B:
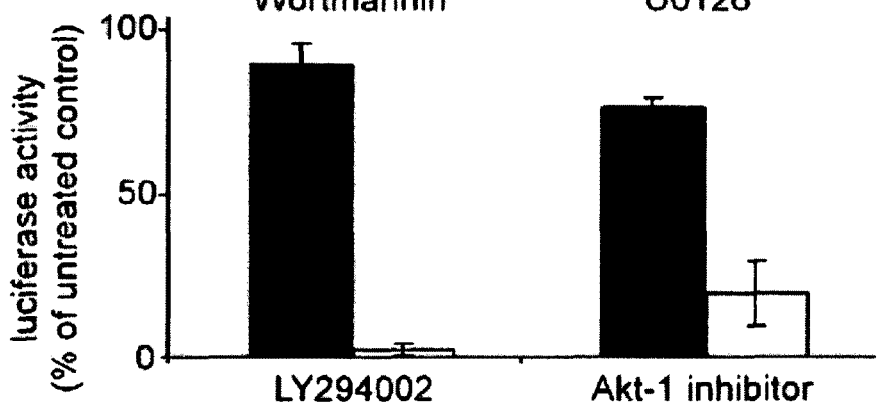
Figure 4C:
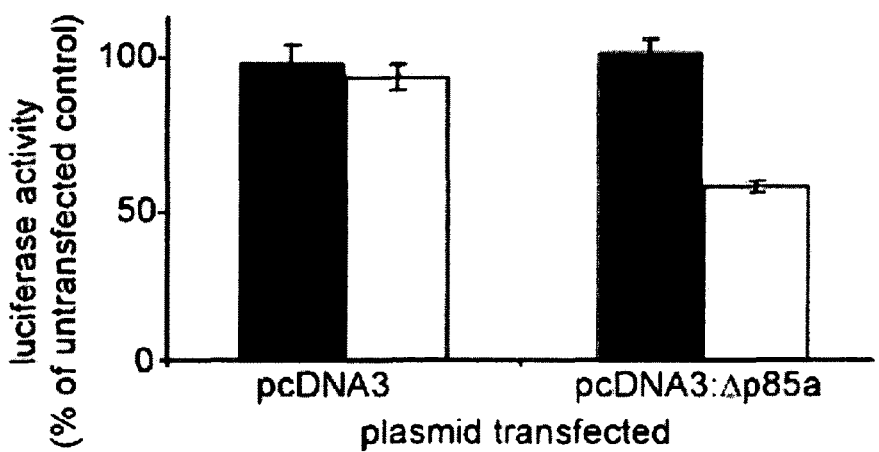
Figure 4D:
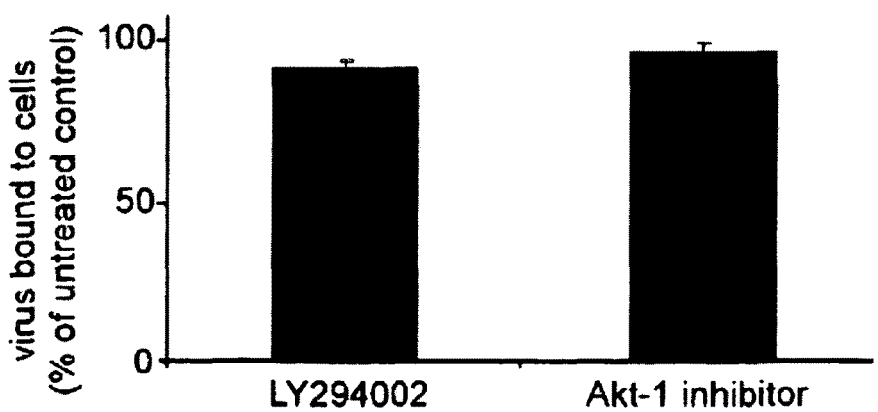

To gain further insight into potential roles that these genes and gene products played in infection, all hits were analyzed using Ingenuity Pathway Analysis software. While this software is primarily designed to identify changes in gene expression patterns using genechips, it was recently used to identify related genes important for intracellular growth of *Salmonella* bacteria. Instead of supplying infection assay data, the probability scores from the RSA analysis were used to prioritize network assignments. This provides an additional filter to remove false positive signals and permit detection for genes that would otherwise be missed using a simple ranking system. A total of 9 networks containing more than 15 genes each were indicated as important for infection by the EBOV pseudotyped virus. Two of the top four networks were related and shared MAP kinases. These gene products are key signaling proteins involved in control of cell growth and proliferation. The remaining networks did not share more than one gene in common. Of the remaining networks, one containing PI3 kinases and another containing calcium/calmodulin dependent kinases were ranked in the top four (FIG. 3). PI3 kinases modulate signaling from membrane bound receptors to promote cell growth, survival and movement. Calcium/calmodulin kinases are key for nerve function and memory but also play important roles in signal transduction to the nucleus through CREB in non-neuronal cells.

A set of canonical, (well characterized) signaling pathways were also indicated as important (Table 1). These contained each of the gene products from the networks discussed above, except for the calcium/calmodulin kinase-containing network. For each of the canonical pathways identified, either MAP kinase or PI3 kinase related gene products were prominent components. Fisher's exact test yielded scores showing a non-random association of each set of hits from the screen with the indicated pathways (Table 1).

TABLE 1

List of canonical pathways and gene product networks identified important for infection by pseudotyped EBOV particles.

| Canonical pathway | Number of siRNA targeting/total genes in network | *p-value |
|---|---|---|
| SAPK/JNK Signaling | 32/147 | $4.1 \times 10^{-25}$ |
| PI3K/AKT Signaling | 30/176 | $2.0 \times 10^{-21}$ |
| Inositol Phosphate metabolism | 26/173 | $6.7 \times 10^{-20}$ |
| Ephrin Receptor Signaling | 32/232 | $9.1 \times 10^{-20}$ |
| ERK/MAPK Signaling | 30/226 | $1.6 \times 10^{-17}$ |
| Other networks | | |
| Calcium/calmodulin signaling | 24/34 | *N.A. |

*p-values were calculated by the Ingenuity Pathways Analysis package for canonical pathways using Fisher's exact test as described in the methods.

To confirm the role of PI3K in Ebola virus infection, cells were treated with the specific PI3K inhibitor LY294002 which was expected to give a similar effect to that seen with siRNA. Cells were plated 1 day prior to each experiment, then they were preincubated with the indicated drug for 1 hr at the indicated dosage before adding the virus. After 1 h preincubation virus was added for another 3 h and then excess drug and virus was removed and virus entry were measured (FIG. 4). The retrovirus pseudotypes were used and luciferase activity used to give a measure of virus entry. To rule out a virus core specific effect, similar studies were performed with vesicular stomatitis virus core to make the pseudotypes using the rapid entry assay. No effect was seen for any of the drugs used. Therefore the impact of PI3k inhibition was specific for Ebola virus.

Figures 5, 6A, 6B, 6C:
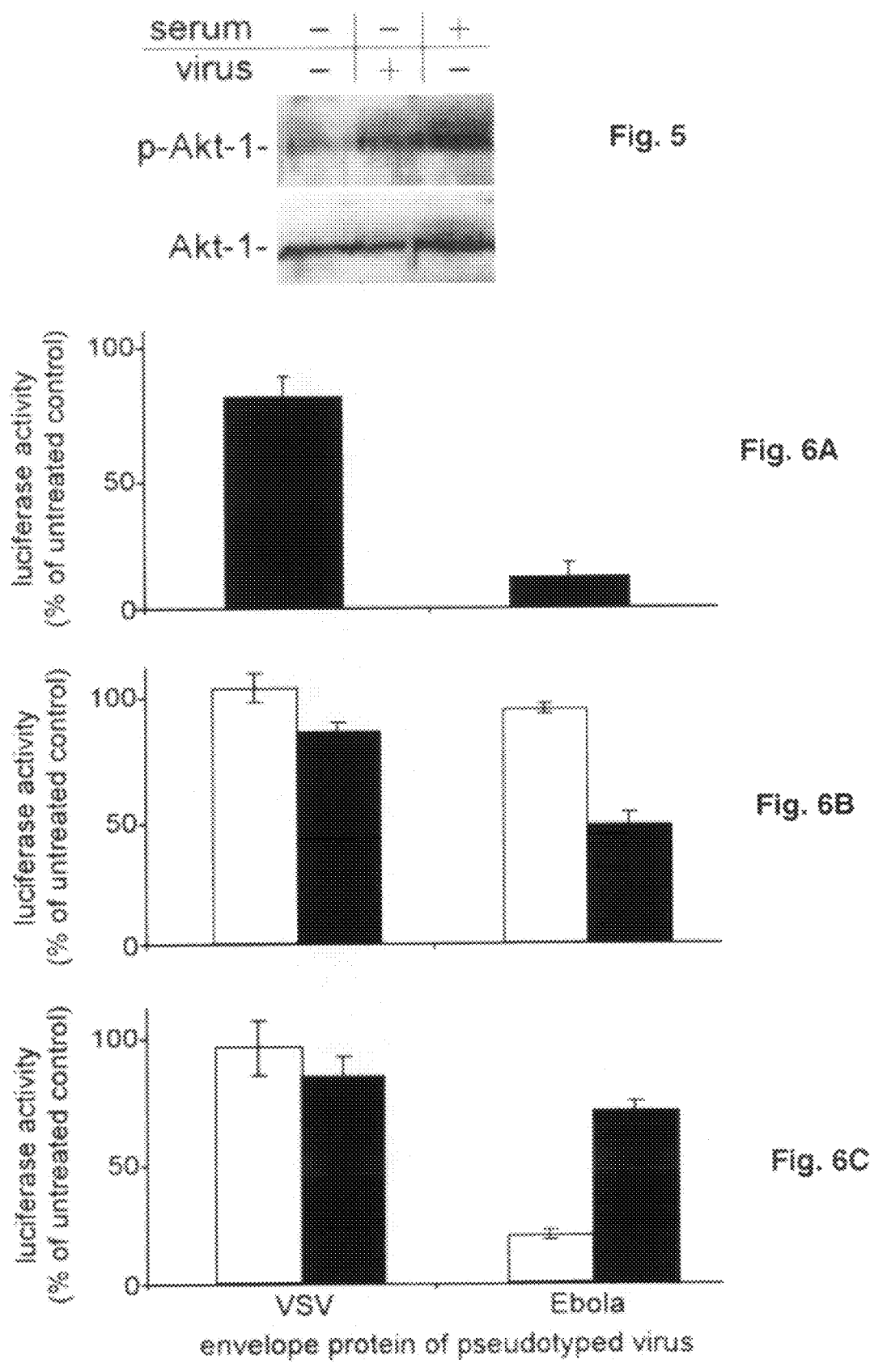

PI3K is an initial signaling molecule in a cascade that leads to stimulation of gene transcription. One the effectors in this pathway is Akt. It was expected then that inhibition of Akt would also lead to inhibition of Ebola virus entry and this was the case (FIG. 4). Akt-1 was also phosphorylated after treatment with Ebola virus particles (FIG. 5). Akt can influence a number of downstream proteins. One of these is Rac-1 which is important for cell cytoskeleton rearrangement. To test that Rac1 was the downstream target of PI3K-Akt activation both a Rac-1 and a dominant negative Rac1 protein were used. Cell treated with drug or expressing the dominant negative protein gave lower entry signals for Ebola virus. VSV entry remained unaffected (FIG. 6).

Example 2

Figures 7, 8:
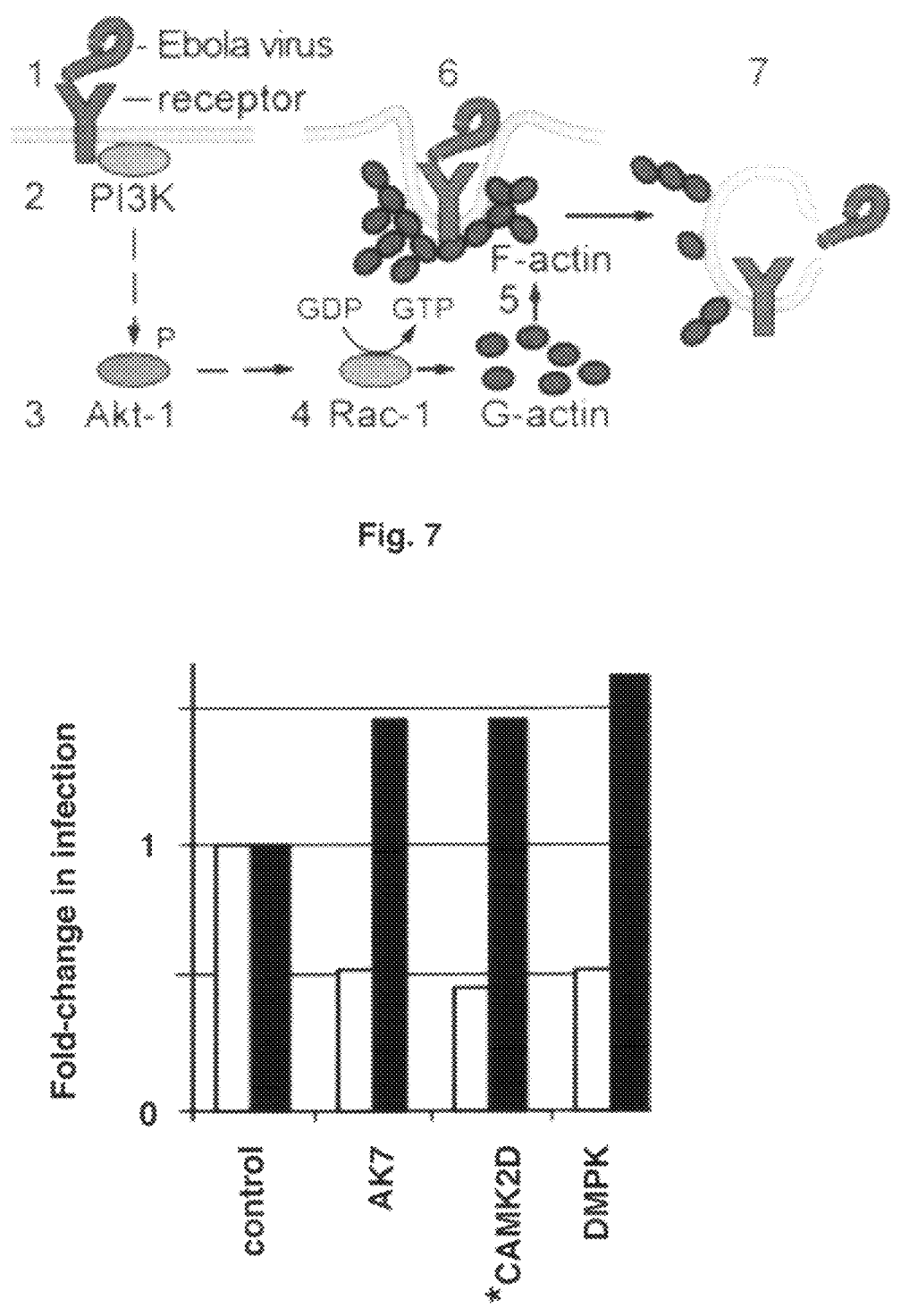

Inhibition of Filovirus Entry into Cells by Blocking a Calcium-Associated Signaling Pathway Human-derived 293 HEK, Hela cells and African green monkey-derived Vero cells, which are generally accepted as good models for study of virus infection of cells in the human body were used herein. Initial work identified the potential role of CAMK2 isoforms in Ebola virus infection by performing an siRNA screen. In this experiment, cells were treated with siRNA targeting cell kinase genes. The activity of genes important for infection by each virus was identified by comparing cells infected with either Ebola Zaire or ecotropic murine leukemia virus (eMLV) env pseudotyped viruses. Since ecotropic murine leukemia virus and Ebola envs have different receptor specificities and functions, differences between the infection activity of each virus indicated specific genes important for the respective virus. The screen was set up to give readout of infection by two independent viruses. Firefly luciferase (fLuc) and Renilla luciferase (RLuc) were used as reporters of infection for Ebola virus and ecotropic murine leukemia virus pseudotypes, respectively. Through this screen CAMK2D was identified as important for Ebola virus infection but did not influence eMLV (FIG. 8).

To confirm the role of CAMK2 in Ebola virus infection, cells were treated with the specific CAMK2 inhibitor KN-93 which was expected to give a similar effect to that seen with CAMK2D siRNA. Cells were plated 1 day prior to each experiment, then they were preincubated with the indicated drug for 1 hr at the indicated dosage before adding the virus. After 1 h preincubation, virus was added for another 1 h and then excess drug and virus was removed by replacing the culture medium. Cells were incubated with drug for another 5 h and then media was replaced to normal and infection was determined by counting infected cells 30 hr later (FIG. 9). Again, the retrovirus pseudotypes were used and luciferase activity used to give a measure of virus infection. To rule out a virus core specific effect similar studies were performed with vesicular stomatitis virus core to make the pseudotypes. This core-encoded green fluorescent protein as the marker of infection. In this case KN-93 activity was compared to the inactive homolog KN-92 (FIG. 9, right). In both cases a strong effect of KN-93 was demonstrated for blocking only the Ebola infection.

Figures 9A, 9B, 10:
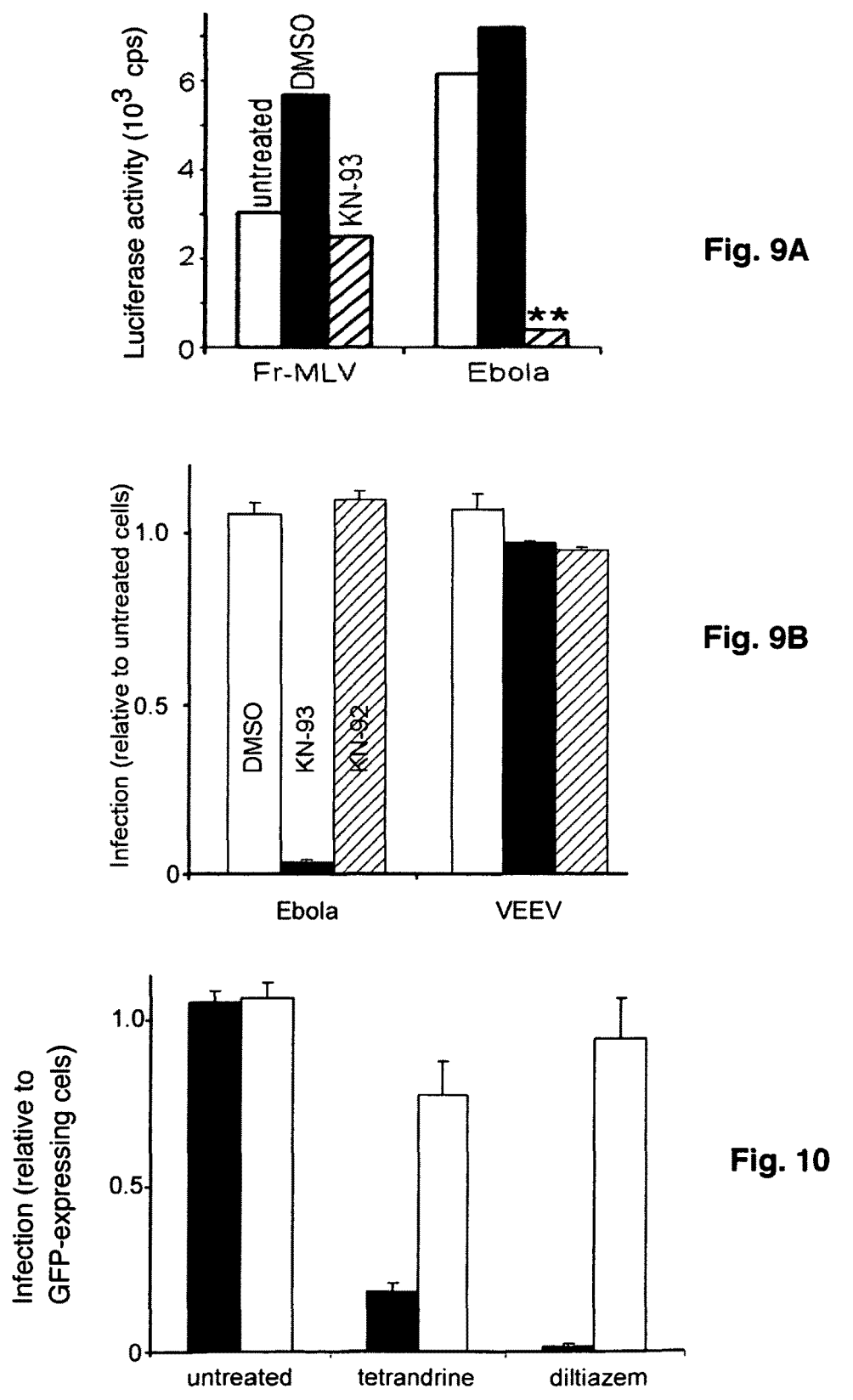
Figures 11A, 11B:
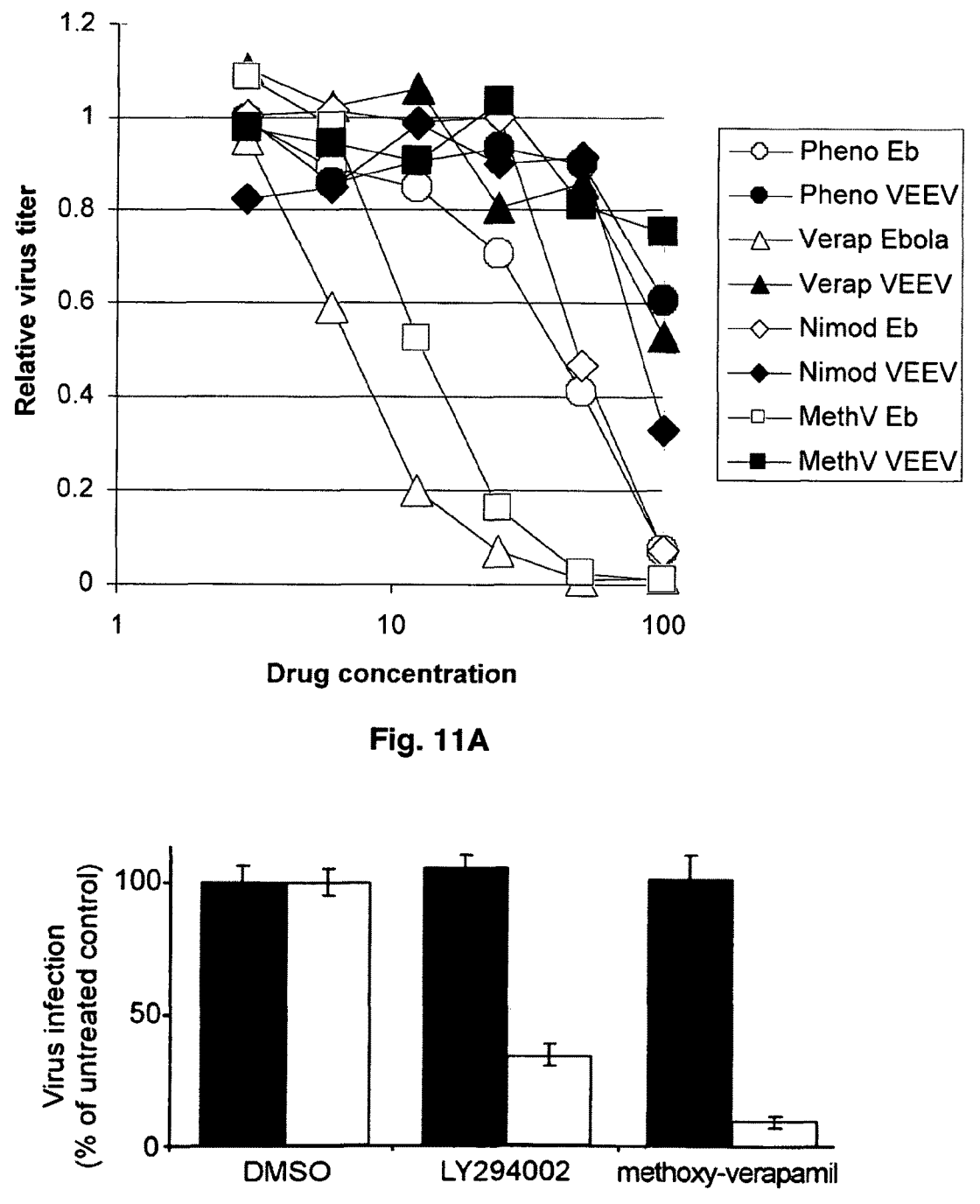

CAMK2 is an intermediary in transcriptional activation through CREB. CAMK2 is typically triggered by calcium influx into the cytoplasm either from internal storage vesicles or from the exterior of the cell. Calmodulin (Calm) acts to recruit and trigger CAMK2 by binding the released calcium. To demonstrate this, the Calmodulin inhibiting drugs, Phenoxybenzamine, W7 and Trifluorperazine were used to treat cells infected with Ebola virus or Venezuelan equine encephalitis virus-like particles. In each case the drugs inhibited Ebola virus but not Venezuelan equine encephalitis virus infection (FIGS. 11A-9B). For the activation of this pathway calcium flow through calcium channels embedded in the cell membrane is an important trigger.

If true, it was expected that calcium channel blocking drugs should specifically inhibit entry of Ebola virus. Calcium channel blocking drugs are one type of commonly prescribed blood pressure medication used by many in the US and other countries. These drugs are collectively termed as dihydropyridines and represent a class of FDA approved drugs that can be taken orally with limited side effects. Initially, two calcium channel blocking drugs, Tetrandine and Diltiazem, were used to test this concept. Cells were treated as for the CAMK2 inhibitor, KN-93 and then infected with VSV core pseudotypes. Venezuelan equine encephalitis virus and Ebola virus envelope particles were compared. As anticipated both drugs proved to be potent and specific blockers of Ebola infection (FIG. 10).

Numerous calcium channel drugs that are specific for each of the 4 classes of channel (L, N, P/Q and R) were also screened. It was observed that that L-type channels elicit the effect seen. Commercially available and FDA approved L-channel blocking drugs were then carefully tested for potency. From this, Verapamil and its derivative Methoxyverapamil were identified as being highly effective against Ebola virus entry. However, Nimodopine and other dihydropyridines were also effective. It is known that transient treatment with each drug is sufficient to irreversibly block Ebola virus entry into cells. This suggests that even a short term usage of such drugs should be effective at preventing Ebola virus infection and spread.

The siRNA profiling coupled with RSA and network analysis predicted the involvement of signaling pathways in EBOV infection. The usefulness of this prediction was tested by treatment of cells with inhibitors of components for two of the identified networks. Drugs that target the catalytic subunit of phosphatidylinositol-3-kinase (PI3K) and calcium/calmodulin kinase 2 (CAMK2) were used. LY294002 inhibits the kinase activity of PI3K and KN-93 prevents association of CAMK2 with calmodulin which is required for its kinase activity. These targets were chosen as they are integral parts of two distinct networks and blocking either of these was predicted to inhibit the function of the entire network for which they are part. Each drug is also highly specific for its substrate, is cell membrane permeable and share low micromolar affinities for their enzyme targets.

Figure 13A:
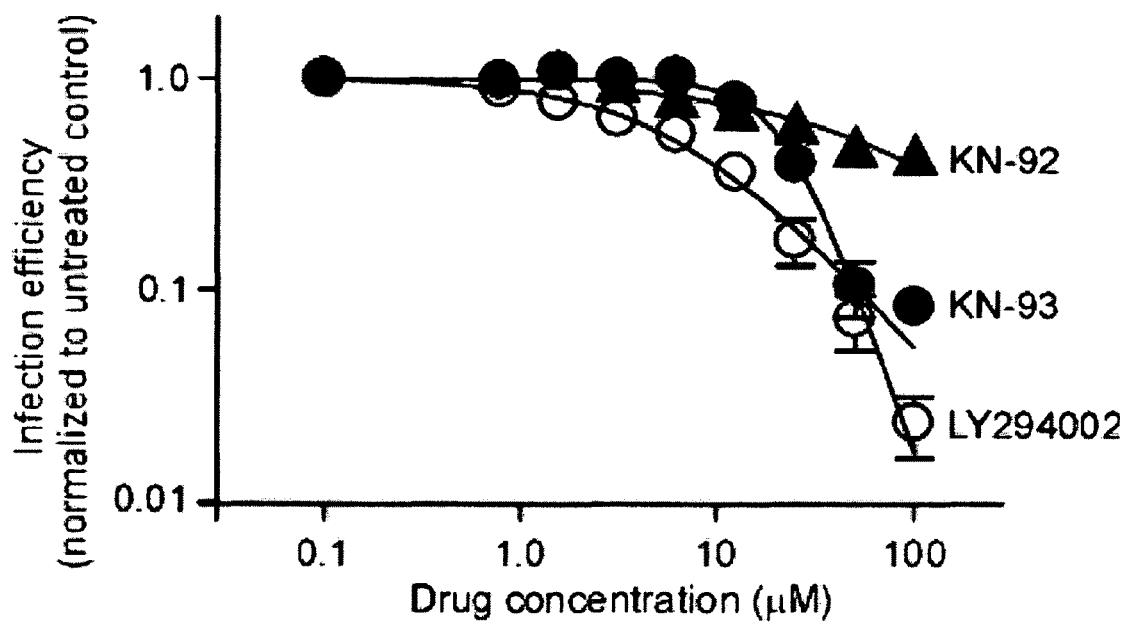
FIG. 13A-13B shows the effects of drug inhibitors of PI3 Kinase and CAMK2 proteins on EBOV pseudotyped virus infection. Cells were treated with LY294002, a specific inhibitor of the PI3K catalytic subunit or KN-93, an inhibitor of CAMK2 or its inactive derivative KN-92.

Each drug was tested for inhibition of infection of the pseudotyped virus using a range of dosages and dose response curves were fitted to the data by non-linear regression (FIG. 13A). LY294002 was most active with a calculated IC50 value for infection of $6.5\pm1.1$ mM ($R^2=0.94$), while KN-93 had an IC50 of $21.4\pm1.1$ mM ($R^2=0.94$). The KN-93 derivative, KN-92, which has much weaker activity against CAMK2, was also tested and was found to be less effective at blocking infection by the pseudotyped virus, only approaching 50% reduction in infection at the highest dose tested (100 mM). These findings suggested that the siRNA profiling had successfully identified two important cell signaling pathways for which activity is required for infection by the pseudotyped virus. However, since a pseudotyped virus was used, the siRNA and drugs may have impacted the expression of the infection marker that was controlled by the lentivirus core.

Figure 13B:
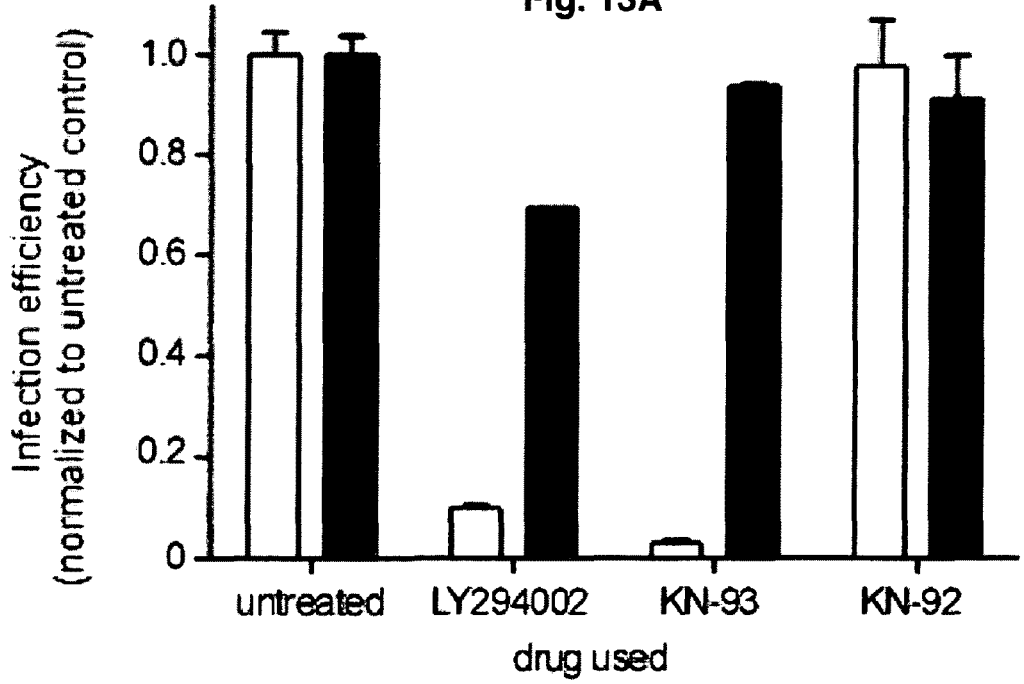

To demonstrate that the drugs were specific for the function of the EBOV envelope proteins and not the lentivirus core, an additional pseudotyped virus was generated and tested. The lentivirus core was substituted for that of vesicular stomatitis virus (VSV). Again, the infection of the VSV core pseudotyped virus was significantly impacted (P<0.001) by either LY294002 or KN-93 but not KN-92 (P>0.05). Since each pseudotype shared a common envelope protein, the activity of the drugs most likely act at an EBOV envelope protein-dependent step in infection. As a final test, the EBOV envelope protein was replaced with that of Venezuelan equine encephalitis virus (VEEV). In contrast to what was seen with the EBOV pseudotyped virus, the VEEV pseudotyped particles were not significantly affected by any of the drugs (P>0.05, FIG. 13B). This finding confirmed that the drugs were specifically affecting the function of the EBOV envelope proteins and not the activity of the pseudotyped virus core.

Figure 14:
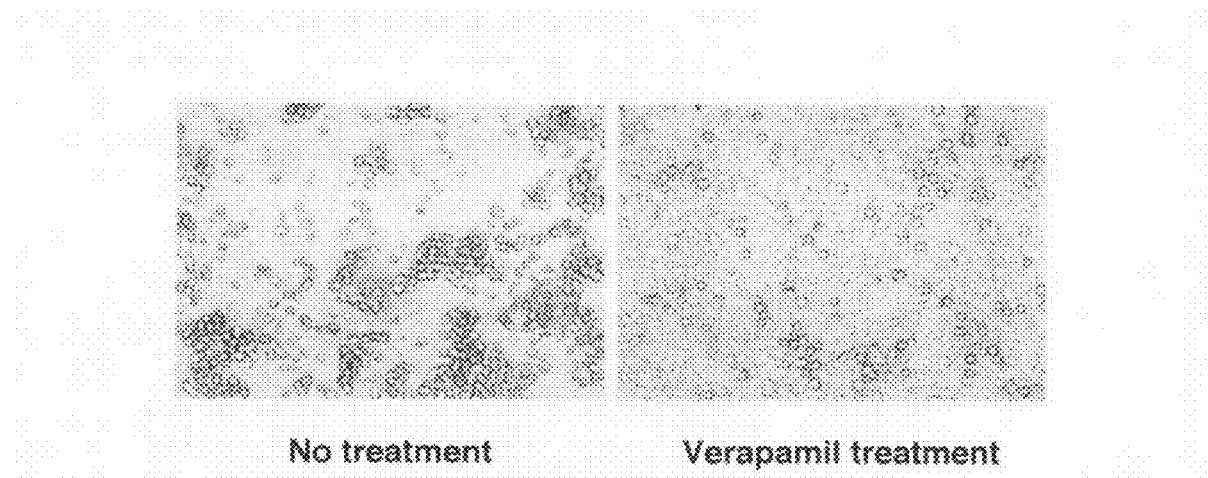
FIG. 14 shows that verapamil protected cells against Ebola virus induced cytopathic effect (CPE). Cells were infected with wild type Ebola virus, Zaire strain, at an MOI of 1, without treatment or in the presence of Verapamil (100 mM). After 7 days images were taken. In the left panel a marked CPE is apparent with many cells rounded up and floating or dead, whereas the cell monolayer remained intact and confluent with treatment.

FIG. 14 shows that verapamil protected cells against Ebola virus induced cytopathic effect. Cells were infected with wild type Ebola virus, Zaire strain, at an MOI of 1, without treatment or in the presence of Verapamil (100 mM). After 7 days images were taken. In the left panel a marked cytopathic effect is apparent with many cells rounded up and floating or dead, whereas the cell monolayer remained intact and confluent with treatment. Thus, treatment with verapamil reduced or significantly prevented the Ebola virus induced cytopathic effect.

Figure 15:
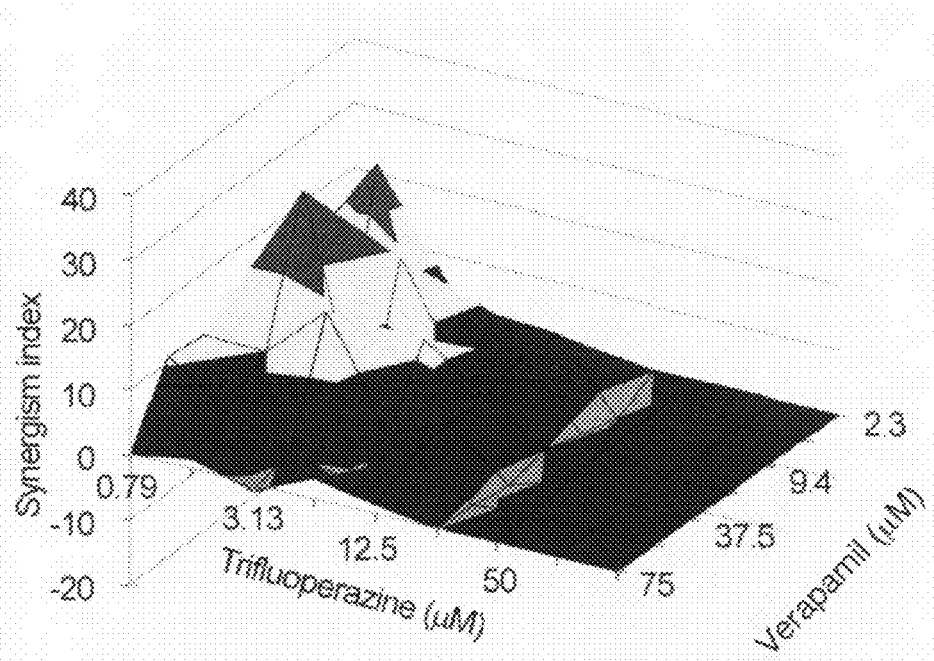
FIG. 15 shows the test for a synergistic inhibitory effect of L-type calcium channel inhibitor (Verapamil) and calmodulin antagonist (Trifluoperazine) on EBOV pseudotyped virus infection. Cells were pretreated with indicated concentrations of Verapamil and Trifluoperazine for 30 minutes and then EBOV pseudotyped virus was added for 6 h, after which medium was replaced with fresh medium. Luciferase activity was measured next day. The extent of syngergism was calculated by the MacSynergy II software package (M. Pritchard, University of Michigan). The graph shows the isobologram for all concentrations tested and peaks indicate strong synergy.

FIG. 15 illustrates the synergistic inhibitory effect of the L-type calcium channel inhibitor (Verapamil) and the calmodulin antagonist (Trifluoperazine) on EBOV pseudotyped virus infection. The graph shows the isobologram for all concentrations tested and peaks indicate strong synergy.

The following references were cited herein:
Baize et al. (1999) Nat Med 5: 423-426.
Baskerville et al., (1978) J Pathol 125: 131-138.
Baskerville et al., (1985) J Pathol 147: 199-209.
Connolly et al. (1999) J Infect Dis 179 Suppl 1: S203-217.
Dolmetsch et al., (2001) Science 294: 333-339.
Feldmann et al., (1993) Arch Virol Suppl 7: 81-100.
Feldmann et al., (1996) Arch Virol Suppl 11:77-100.
Fisher-Hoch and McCormick (1999) Curr Top Microbiol Immunol 235: 117-143.
Geisbert et al. (2000) Lab Invest 80: 171-186.
Mupapa et al., (1999) J Infect Dis 179 Suppl 1: S18-23.
Nabel G J (1999) Nat Med 5: 373-374.
Peters C J (1996) West J Med 164: 36-38.
Peters and LeDuc (1999) J Infect Dis 179 Suppl 1: ix-xvi.
Sadek et al., (1999) J Infect Dis 179 Suppl 1: S24-27.
Schnittler and Feldmann (1999) Curr Top Microbiol Immunol 235: 175-204.
Schnittler et al., (1993) J Clin Invest 91: 1301-1309.
Schnittler and Feldmann (1998) Clin Infect Dis 27: 404-406.
Simmons et al., (2002) J Virol 76: 2518-2528.
Stroher et al. (2001) J Virol 75: 11025-11033.
World Health Organization (2004). 103 103. 1-2 p.
Xu et al. (1998) Nat Med 4: 37-42.
Yang et al. (1998) Science 279: 1034-1037.
Yang et al. (2000) Nat Med 6: 886-889.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of treating filovirus infection in an individual infected with a filovirus consisting essentially of:
administering a pharmacologically effective amount of an L-type calcium channel blocker, thereby treating the individual infected with the filovirus, wherein the L-type calcium channel blocker is Verapamil or methoxyverapamil.

2. The method of claim 1, wherein said filovirus is an Ebola virus or a Marburg virus.

* * * * *